United States Patent
Hay et al.

(10) Patent No.: US 8,895,068 B2
(45) Date of Patent: *Nov. 25, 2014

(54) NANOPARTICLE COMPOSITION AND ASSOCIATED METHODS THEREOF

(75) Inventors: Bruce Allan Hay, Niskayuna, NY (US); Brian Christopher Bales, Niskayuna, NY (US); Michael Todd Luttrell, Clifton Park, NY (US); Binil Itty Ipe Kandapallil, Mechanicville, NY (US)

(73) Assignee: General Electric Company, Niskayuna, NY (US)

( * ) Notice: Subject to any disclaimer, the term of this patent is extended or adjusted under 35 U.S.C. 154(b) by 474 days.

This patent is subject to a terminal disclaimer.

(21) Appl. No.: 12/968,577

(22) Filed: Dec. 15, 2010

(65) Prior Publication Data

US 2012/0156141 A1 Jun. 21, 2012

(51) Int. Cl.
| | | |
|---|---|---|
| *A61K 9/14* | (2006.01) | |
| *A61B 5/055* | (2006.01) | |
| *B82Y 15/00* | (2011.01) | |
| *A61K 49/18* | (2006.01) | |
| *B82Y 30/00* | (2011.01) | |
| *B82Y 5/00* | (2011.01) | |
| *B82Y 40/00* | (2011.01) | |

(52) U.S. Cl.
CPC ............. *A61K 49/1842* (2013.01); *B82Y 15/00* (2013.01); *A61K 49/1845* (2013.01); *B82Y 30/00* (2013.01); *B82Y 5/00* (2013.01); *B82Y 40/00* (2013.01)
USPC .............. 424/489; 424/9.1; 424/9.3; 424/493

(58) Field of Classification Search
CPC ....... A61K 9/51; A61K 9/5107; A61K 49/00; A61K 49/06; A61K 49/08; A61K 49/101
USPC ............................ 424/465–489, 9.1, 9.3, 493
See application file for complete search history.

(56) References Cited

U.S. PATENT DOCUMENTS

| | | |
|---|---|---|
| 5,160,725 A | 11/1992 | Pilgrimm |
| 5,213,788 A | 5/1993 | Ranney |
| 5,464,696 A | 11/1995 | Tournier et al. |
| 5,597,531 A | 1/1997 | Liberti et al. |
| 5,916,539 A * | 6/1999 | Pilgrimm .................... 424/9.322 |
| 6,274,121 B1 | 8/2001 | Pilgrimm |
| 6,423,296 B1 | 7/2002 | Gunther et al. |
| 7,179,449 B2 | 2/2007 | Lanza et al. |
| 7,727,969 B2 | 6/2010 | Farokhzad et al. |
| 2003/0170308 A1* | 9/2003 | Cleary et al. .................. 424/486 |
| 2004/0253181 A1 | 12/2004 | Port et al. |
| 2007/0281034 A1 | 12/2007 | Kirpotin et al. |
| 2008/0213189 A1* | 9/2008 | Lee et al. ..................... 424/9.32 |
| 2009/0226376 A1 | 9/2009 | Grimmond et al. |
| 2010/0221346 A1 | 9/2010 | Plank et al. |

FOREIGN PATENT DOCUMENTS

| | | |
|---|---|---|
| WO | 2009051392 A2 | 4/2009 |
| WO | 2011051422 A2 | 5/2011 |

OTHER PUBLICATIONS

Marco et al., "Physicochemical Characterization of Ultrasmall Superparamagnetic Iron Oxide Particles (USPIO) for Biomedical Application as MRI Contrast Agents", International Journal of Nanomedicine, vol. 2, Issue 4, pp. 609-622, Dec. 2007.

Qiao et al., "Superparamagnetic Iron Oxide Nanoparticles: from Preparations to In Vivo MRI Applications", Journal of Materials Chemistry, vol. 19, Issue 35, pp. 6274-6293, 2009.

David Portet et al; "Nonpolymeric Coatings of Iron Oxide Colloids for Biological Use as Magnetic Resonance Imaging Contrast Agents"; Journal of Colloid and Interface Science 238, 37-42 (2001) doi:10.1006/jcis.2001.7500, available online at http://www.idealibrary.com; 6 Pages.

Search Report and Written Opinion from corresponding PCT Application No. PCT/EP2011/072676 dated Apr. 25, 2012.

* cited by examiner

*Primary Examiner* — Michael G Hartley
*Assistant Examiner* — Micah-Paul Young
(74) *Attorney, Agent, or Firm* — Andrew J. Caruso

(57) ABSTRACT

A nanoparticle composition is provided, wherein the composition comprises a nanoparticulate metal oxide; and a phosphorylated polyol comprising at least two phosphate groups. The polyol comprises one or more hydrophilic groups selected from the group consisting of polyethylene ether moieties, polypropylene ether moieties, polybutylene ether moieties, and combinations of two or more of the foregoing hydrophilic moieties. A method of making the nanoparticle composition is also provided. The nanoparticle compositions provided by the present invention may be used as contrast agents in medical imaging techniques such as X-ray and magnetic resonance imaging.

8 Claims, 1 Drawing Sheet

NANOPARTICLE COMPOSITION AND ASSOCIATED METHODS THEREOF

BACKGROUND

This invention relates generally to nanoparticle compositions which form stable aqueous suspensions, particularly nanoparticle compositions based on transition metal oxides. Such nanoparticle compositions are useful for a variety of applications including diagnostic imaging.

Nanoparticles, i.e. particles whose diameters are appropriately measured in nanometers, have been considered for a wide variety of end uses. Some of the uses require a substantial degree of hydrophilicity. However, in a number of instances, the material upon which nanoparticles are based may lack this attribute. For instance, nanoparticles with appropriate imaging properties for use as contrast agents for MR and/or X-ray imaging are typically based on transition metal oxides which lack the level of hydrophilicity required to form the stable aqueous suspensions needed for such applications. Therefore, efforts have been made to modify the surface properties of such nanoparticles to be more compatible with aqueous media and thereby enhance the stability of aqueous suspensions of such nanoparticles. In some applications, it is also desirable that the nanoparticles have a relatively monodisperse particle size distribution. However, such surface treatments typically result in a relatively polydisperse particle size distribution.

Typically, nanoparticle compositions in aqueous suspension are subject to agglomeration and precipitation of the constituent nanoparticles. Surface treatments may be used to inhibit such agglomeration and precipitation, and may take the form of adding one or more stabilizer substances to a suspension of a nanoparticulate core species in a diluent. Such stabilizer substances are thought to attach to the surface of the suspended nanoparticulate core species and to form a barrier (or shell) interposed between at least a portion of the surface of the nanoparticulate core species and the diluent in which the nanoparticulate core species are suspended.

Formulations comprising nanoparticle compositions suitable for use in medical imaging applications typically require purification prior to presentation to a subject. The various purification techniques employed may degrade the hydrophilicity of the nanoparticle composition and may alter the particle size distribution of the nanoparticle composition. Prudent medical practice and logic strongly suggest that formulations containing nanoparticle compositions to be used as contrast agents for in vivo use in human subjects will be subjected to rigorous purification and be required to exhibit robust suspension stability in isotonic aqueous media, for example in 150 mM sodium chloride solution.

Thus, there is a need for nanoparticle compositions with improved properties, particularly related to increased hydrophilicity, stability in colloidal suspension, and enhanced safety.

BRIEF DESCRIPTION

In one embodiment the present invention provides a nanoparticle composition comprising a nanoparticulate metal oxide; and a phosphorylated polyol comprising at least two phosphate groups, wherein the polyol comprises one or more hydrophilic groups selected from the group consisting of polyethylene ether moieties, polypropylene ether moieties, polybutylene ether moieties, and combinations of two or more of the foregoing hydrophilic moieties.

In another embodiment, the present invention provides a nanoparticle composition comprising a nanoparticulate iron oxide core; and a shell comprising a phosphorylated polyol comprising at least two phosphate groups, wherein at least two of the phosphate groups occupy positions in the phosphorylated polyol which constitute a 1, 2 or 1,3 spatial relationship to one another and the polyol comprises a hydrophilic group selected from the group consisting of polyethylene ether moieties, polypropylene ether moieties, polybutylene ether moieties, and combinations of two or more of the foregoing hydrophilic moieties.

In yet another embodiment, the present invention provides a nanoparticle composition comprising a nanoparticulate metal oxide core, wherein the metal oxide comprises a metal selected from the group consisting of iron, tantalum, zirconium, and hafnium; and a shell comprising a phosphorylated polyol comprising at least two phosphate groups, wherein at least two of the phosphate groups occupy positions in the phosphorylated polyol which constitute a 1, 2 or 1,3 spatial relationship to one another and the polyol comprises a hydrophilic group selected from the group consisting of polyethylene ether moieties, polypropylene ether moieties, polybutylene ether moieties, and combinations of two or more of the foregoing hydrophilic moieties.

In yet another embodiment, the present invention provides a process for making a nanoparticle composition comprising contacting a nanoparticulate metal oxide core with a shell composition comprising a phosphorylated polyol comprising at least two phosphate groups and one or more hydrophilic groups selected from the group consisting of polyethylene ether moieties, polypropylene ether moieties, polybutylene ether moieties, and combinations of two or more of the foregoing hydrophilic moieties.

BRIEF DESCRIPTION OF THE DRAWING FIGURES

These and other features, aspects, and advantages of the present invention will become better understood when the following detailed description is read with reference to the accompanying drawings in which like characters represent like parts throughout the drawings, wherein.

DETAILED DESCRIPTION

Figure 1:
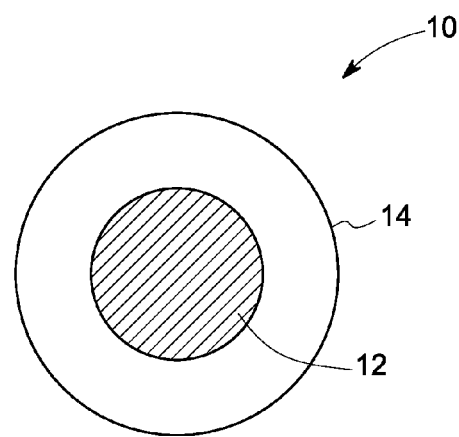
FIG. 1 is an idealized cross sectional view of a nanoparticle comprising a core and a shell, in accordance with one embodiment of the present invention.

In the following specification and the claims which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

Unless specified otherwise, as used herein the term "phosphate group" refers to the bracketed group I shown below (and its ionized forms II and III) and includes four constituent oxygen atoms and one constituent phosphorous atom but does not include the carbon atom shown. The phosphate group is linked through one of its four oxygen atoms via a bond (see dashed line) to a carbon atom in an organic moiety, the phosphate group and the organic moiety forming constituents of an organic molecule, for example a phosphorylated polyol (See illustrative examples in the Experimental Section of this disclosure). Because phosphate groups readily ionize to the corresponding mono anionic (See group II) and dianionic (See group III) forms, the term phosphate group as used herein includes each of these forms in addition to the fully protonated form featured in group I. The relative amounts of each of the forms I-III of a phosphate group present in, for example, a phosphorylated polyol, will depend on the environment in which the phosphate group is present. At high pH in aqueous media there should be more of form III relative to form I, for example. In addition, for the purposes of this disclosure, the term

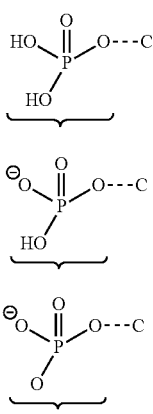

phosphate group specifically excludes "polyphosphates" in which a first phosphorous atom is linked to a second phosphorous atom via an oxygen atom without an intervening carbon atom. Structure IV below illustrates a polyphosphate as defined herein. As defined herein, a polyphosphate comprises a first phosphorous atom ($P^1$) linked to a second phosphorous atom ($P^2$) via an oxygen atom without an intervening carbon atom. In the polyphosphate illustrated in structure IV the

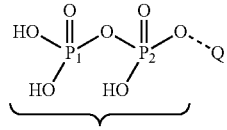

polyphosphate group comprises seven oxygen atoms and two phosphorous atoms. An alternate illustrative polyphosphate group includes ten oxygen atoms and three phosphorous atoms. As illustrated in structure IV a polyphosphate group is linked to a moiety Q which may be an organic moiety or an inorganic moiety. Polyphosphoric acid illustrates an example of a polyphosphate in which Q is an inorganic moiety. Trisodium O-methyl diphosphate illustrates an organic diphosphate wherein Q is a methyl group and the OH groups attached to phosphorous are ionized and attended by charge-balancing counterions (three sodium cations) (Chemical Papers 62 (2) 223-226 (2008)). Those of ordinary skill in the art will appreciate that as defined herein, the term polyphosphate encompasses both "acyclic polyphosphates" (wherein neither of the first phosphorous atom ($P^1$) linked to the second phosphorous atom ($P^2$) via an oxygen atom without an intervening carbon atom is part of a cyclic structure) and "cyclic polyphosphates" (wherein in which at least one of the first phosphorous atom ($P^1$) linked to the second phosphorous atom ($P^2$) via an oxygen atom without an intervening carbon atom is part of a cyclic structure). Those of ordinary skill in the art will further appreciate that there are various ionized forms of polyphosphates and that the term polyphosphate is meant to include the ionized forms of an idealized fully protonated polyphosphate, for example the fully protonated polyphosphate structure shown in structure IV above.

As discussed in detail below, embodiments of the present invention include a nanoparticle composition comprising a nanoparticulate metal oxide, and a phosphorylated polyol, wherein the phosphorylated polyol comprises at least two phosphate groups and a hydrophilic group, wherein the phosphate groups are chemically and sterically accessible to the metal oxide and the hydrophilic group is selected from the group consisting of polyethylene ether moieties, polypropylene ether moieties, polybutylene ether moieties, and combinations of two or more of the foregoing hydrophilic moieties.

In various embodiments, the nanoparticle compositions provided by the present invention are sufficiently hydrophilic to form stable aqueous colloidal suspensions that exhibit no substantial change in the hydrodynamic diameter ($D_H$) of constituent nanoparticles over a prolonged time frame (e.g. over several days to several weeks). A change in hydrodynamic diameter over time is a key indicator of colloidal suspension stability. Thus, nanoparticle compositions that display robust stability in colloidal suspension should show little or no increase in the hydrodynamic diameter ($D_H$) of the suspended constituent nanoparticles over the time period of interest. Hydrodynamic diameter may be measured by dynamic light scattering (DLS). Those of ordinary skill in the art will understand that the term hydrodynamic diameter ($D_H$) refers to the average hydrodynamic diameter.

As used herein, the term 'nanoparticle composition' refers to a composition comprising constituent nanoparticles having average particle size of less than 1 micrometer. As used herein, the term 'size' refers to the hydrodynamic diameter of the nanoparticles. In one embodiment, the nanoparticle composition provided by the present invention has a $D_H$ in a of range from about 2 nm to about 500 nm. In an alternate embodiment, the nanoparticle composition provided by the present invention has a $D_H$ in a range of from about 10 nm to 25 nm. In one embodiment, the nanoparticle composition provided by the present invention has a $D_H$ of less than 50 nm. In another embodiment, the nanoparticle composition provided by the present invention has a $D_H$ of less than 10 nm. In yet another embodiment, the nanoparticle composition provided by the present invention has a $D_H$ of less than 5 nm. A small particle size may be advantageous in, for example, facilitating clearance of the nanoparticle composition from the kidneys and other organs of a subject following a medical imaging procedure employing the nanoparticle composition as a contrast agent.

In one embodiment, the nanoparticle composition provided by the present invention comprises a core-shell structure, wherein the core comprises a nanoparticulate metal oxide, and the shell comprises a phosphorylated polyol comprising at least two phosphate groups and one or more hydrophilic groups selected from the group consisting of polyethylene ether moieties, polypropylene ether moieties, polybutylene ether moieties, and combinations of two or more of the foregoing hydrophilic moieties.

In various embodiments, the shell comprising the phosphorylated polyol stabilizes the nanoparticulate metal oxide core and prevents the formation of larger metal oxide particles by association (agglomeration) of the nanoparticulate metal oxide core particles. One or more embodiments of the invention are related to a nanoparticle composition having the idealized core-shell structure shown in FIG. 1. The nanoparticle composition 10 comprises a nanoparticulate metal oxide core 12, and a shell 14 comprising a phosphorylated polyol as described herein. In one embodiment, the present invention provides a nanoparticle composition characterized by its ability to form a stable aqueous colloidal suspension that exhibits no substantial change in hydrodynamic diameter ($D_H$) as determined by dynamic light scattering in 150 mM aqueous NaCl after tangential flow filtration and storage for one week at room temperature.

The metal oxide core of the nanoparticle composition provided by the present invention has dimensions appropriately measured in nanometers. In various embodiments, the nanoparticulate metal oxide core may be prepared as a suspension in a diluent and the hydrodynamic diameter of the suspended nanoparticulate metal oxide core particles may be measured, for example by dynamic light scattering. In one embodiment, the nanoparticulate metal oxide core has a $D_H$ as measured by dynamic light scattering in a range from about 1 nm to about 30 nm. In an alternate embodiment, the nanoparticulate metal oxide core has a $D_H$ as measured by dynamic light scattering of about 5 nm. In one or more embodiments, the nanoparticulate metal oxide core comprises a nanoparticulate super paramagnetic iron oxide (SPIO) and has a $D_H$ as measured by dynamic light scattering of less than about 25 nm.

The nanoparticulate metal oxide core typically comprises a transition metal oxide. In one embodiment, the nanoparticulate metal oxide core consists of a single transition metal oxide, for example tantalum oxide alone or iron oxide alone. In another embodiment, the nanoparticulate metal oxide core comprises two or more transition metal oxides. Thus in one embodiment the nanoparticulate metal oxide core comprises both tantalum oxide and hafnium oxide. In various embodiments, the nanoparticulate metal oxide core may comprise additional materials not constituting metal oxides, such as metal nitrides and metal sulfides. Thus, in one embodiment the nanoparticulate metal oxide comprises tantalum oxide and hafnium nitride. In yet another embodiment, the nanoparticulate metal oxide core comprises tantalum oxide and tantalum sulfide.

In one embodiment, the nanoparticulate metal oxide core comprises a transition metal oxide selected from the group consisting of oxides of tungsten, tantalum, hafnium, zirconium, zinc, molybdenum, silver, iron, manganese, copper, cobalt, nickel and combinations of two or more of the foregoing transition metal oxides. In one specific embodiment, the transition metal oxide is tantalum oxide. In an alternate embodiment, the transition metal oxide is iron oxide. Typically, the nanoparticulate metal oxide core comprises at least 30% by weight of the transition metal component of the transition metal oxide. In one embodiment, the nanoparticulate metal oxide core comprises at least 50% by weight of the transition metal component. In yet another embodiment, the nanoparticulate metal oxide core comprises at least 75% by weight of the transition metal component. Those of ordinary skill in the art will appreciate that a relatively high transition metal content in the nanoparticulate metal oxide core can provide nanoparticle compositions with a relatively higher degree of radiopacity per unit volume, thereby imparting more efficient performance as a contrast agent.

For use as X-ray contrast agents, the nanoparticle composition provided by the present invention should be substantially more radiopaque than the tissue and bone matter typically found in living organisms. In certain embodiments, the present invention provides nanoparticle compositions comprising nanoparticulate metal oxide cores comprising metal atoms having an atomic number greater than or equal to 34. Such nanoparticle compositions may be effective as imaging agents when presented to a subject in a medical imaging formulation having a nanoparticle composition concentration sufficient to provide an effective metal concentration in the subject's blood during the imaging procedure of approximately 50 mM. Such materials are likely yield appropriate contrast enhancement of about 30 Hounsfield units (HU) or greater. Of special interest are materials that lead to a contrast enhancement in a range from about 100 Hounsfield to about 5000 Hounsfield units. Examples of transition metal elements that may provide this property include tungsten, tantalum, hafnium, zirconium, molybdenum, silver, and zinc. In one embodiment, the present invention provides a nanoparticle composition suitable for use in X-ray imaging applications such as computed tomography (CT), the nanoparticle composition comprising a nanoparticulate metal oxide core comprising tantalum oxide.

In one or more embodiments, the core of the nanoparticle composition comprises tantalum oxide with a particle size up to about 6 nm. Such embodiments may be particularly attractive in imaging techniques that apply X-rays to generate imaging data, due to the high degree of radiopacity of the tantalum-containing core and the small size that aids rapid renal clearance, for example.

In some embodiments, the metal oxide core comprises a transition metal, which exhibits magnetic behavior, including, for example, superparamagnetic behavior. In some embodiments, the metal oxide core comprises a paramagnetic metal, selected from the group consisting of iron, manganese, copper, cobalt, nickel, and combinations thereof. In a specific embodiment, the metal oxide core comprises superparamagnetic iron oxide (SPIO). In one embodiment, the iron oxide is doped with another metal.

In some embodiments, the nanoparticle compositions of the present invention may be used as magnetic resonance (MR) contrast agents. For use as MR contrast agents the nanoparticle composition provided by the present invention advantageously comprises a paramagnetic metal species, with those compositions that comprise a superparamagnetic metal species being of particular interest. Examples of potential paramagnetic and superparamagnetic materials include materials comprising one or more of iron, manganese, copper, cobalt, nickel or zinc. A particularly interesting group of materials are those based upon iron oxide, especially SPIO's, which typically comprise from about 65% to about 75% iron by weight. In one embodiment, the nanoparticulate metal oxide core comprises a iron compound having general formula $[Fe_2^+O_3]_x[Fe_2^+O_3(M^{2+}O)]_{1-x}$ wherein $1 \geq x \geq 0$ and $M^{2+}$ is a metal cation such as cations of iron, manganese, nickel, cobalt, magnesium, copper, zinc and a combination of such cations. Examples of iron compounds falling within the scope of this general formula include magnetite ($Fe_3O_4$) when the metal cation ($M^{2+}$) is ferrous ion ($Fe^{2+}$) and x=0; and maghemite ($\gamma$-$Fe_2O_3$) when x=1.

As shown in the idealized structure shown in FIG. 1, the nanoparticle composition may comprise a shell which completely covers the nanoparticulate metal oxide core. Thus, in certain embodiments, the nanoparticle composition is said to comprise a shell which substantially covers the core. As used herein, the term "substantially covers" means that a percentage surface coverage of the core by the shell is greater than about 20%. As used herein, the term percentage surface coverage refers to the ratio of the core surface covered by the shell to the core surface not covered by the shell. In some embodiments, the percentage surface coverage of the nanoparticle may be greater than about 40%.

In some embodiments, the shell may facilitate improved water solubility, reduce aggregate formation, prevent oxidation of nanoparticles, maintain the uniformity of the core-shell entity, and/or provide biocompatibility for the nanoparticle compositions.

The average thickness of shell is typically in a range from about 1 to about 50 nm. In one embodiment, the shell has an average thickness less than 50 nm. In another embodiment, the shell has an average thickness of less than 8 nm. In yet another embodiment, the shell has an average thickness of less than 5 nm.

The nanoparticle compositions provided by the present invention may comprise more than one shell layer disposed on the nanoparticulate metal oxide core. By judicious selection of processing conditions, a nanoparticulate metal oxide core species may be prepared as a suspension in a diluent and thereafter treated under a first set of conditions with one or more stabilizer substances to generate a first nanoparticle composition comprising a first shell, and thereafter the first nanoparticle composition is treated under a second set of conditions with one or more different stabilizer substances which generate a second nanoparticle composition comprising both the first shell and a second shell. In embodiments comprising a plurality of shells, at least one of the shells comprises a phosphorylated polyol comprising at least two phosphate groups and one or more hydrophilic groups selected from the group consisting of polyethylene ether moieties, polypropylene ether moieties, polybutylene ether moieties, and combinations of two or more of the foregoing hydrophilic moieties. In one embodiment, a single shell may cover essentially the entire surface of the nanoparticulate metal oxide core. In another embodiment, the present invention provides a nanoparticle composition comprising a single nanoparticulate metal oxide core composition and multiple shell compositions, as in the case where a nanoparticulate metal oxide core species is prepared as a suspension in a diluent, the suspension is divided in half and each half is treated with a different phosphorylated polyol, and subsequently the halves are recombined. Thus, within a nanoparticle composition provided by the present invention, individual particles may comprise shells which are essentially identical to the shells of companion particles within the nanoparticle composition; or the shells of constituent particles within the nanoparticle composition may differ from one another in composition.

As noted, the nanoparticle compositions provided by the present invention comprise a phosphorylated polyol, the phosphorylated polyol comprising at least two phosphate groups and one or more hydrophilic groups. The hydrophilic group (or groups) is selected from the group consisting of polyethylene ether moieties, polypropylene ether moieties, polybutylene ether moieties, and combinations of two or more of the foregoing hydrophilic moieties. Polyethylene ether moieties are defined as moieties comprising oxyethyleneoxy structural units —$OCH_2CH_2O$—, and/or substituted oxyethyleneoxy structural units. For convenience and because of the close structural association with the term polyethylene glycol (PEG), such moieties may at times herein be referred to as PEG groups, or PEG moieties, and are characterized by a moiety molecular weight. Illustrative polyethylene ether moieties are given in Table 1 below and throughout this disclosure. Similarly, polypropylene ether moieties are defined as moieties comprising oxypropyleneoxy structural units —$OCH_2CH_2CH_2O$— and/or substituted oxypropyleneoxy structural units. For convenience polypropylene ether moieties may at times herein be referred to as polypropylene glycol groups or moieties. Similarly, polybutylene ether moieties are defined as moieties comprising oxybutyleneoxy structural units —$OCH_2CH_2CH_2CH_2O$— and/or substituted oxybutyleneoxy structural units. For convenience polybutylene ether moieties may at times herein be referred to as poly-THF moieties.

Illustrative phosphorylated polyols used in, and provided by the present invention are given in Table 1 below. In each of Entries 1a-1f, the illustrated phosphorylated polyol comprises at least two phosphate groups and one or more hydrophilic groups selected from the group consisting of one or more of a polyethylene ether moieties, polypropylene ether moieties, polybutylene ether moieties, and combinations of two or more of the foregoing hydrophilic moieties.

TABLE 1

Exemplary Phosphorylated Polyols and Constituent Structural Elements

Entry  Structure of Phosphorylated Polyol

1a

TABLE 1-continued
Exemplary Phosphorylated Polyols and Constituent Structural Elements
Entry  Structure of Phosphorylated Polyol
1b
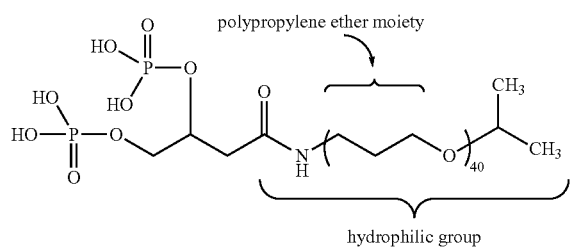
1c
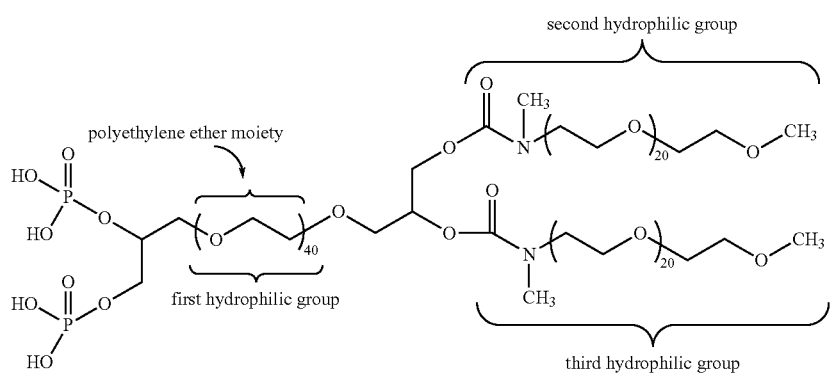
1d
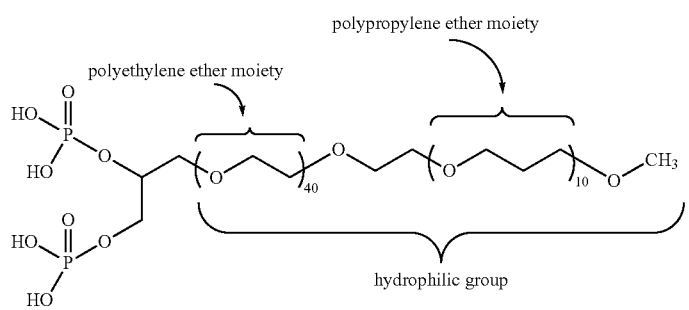
1e
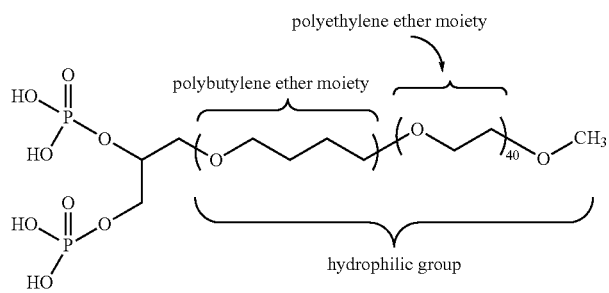
1f
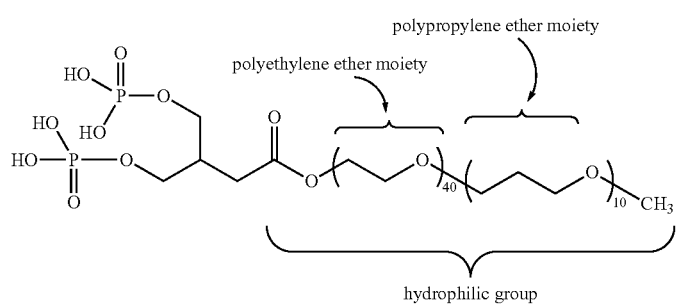

As will be appreciated by those of ordinary skill in the art the phosphate groups present in the phosphorylated polyol may be configured such that two phosphate groups within the same phosphorylated polyol occupy positions which constitute a 1,2; 1,3; 1,4; 1,5; or 1,6 spatial relationship to one another. In Table 1 Example 1a illustrates a phosphorylated polyol in which two phosphate groups are configured in a 1,3 spatial relationship with respect to each other. Example 1b illustrates a phosphorylated polyol in which two phosphate groups are configured in a 1,2 spatial relationship with respect to each other. Those of ordinary skill in the art will be familiar with such distinctions. A 1,2 spatial relationship of the at least two phosphate groups includes embodiments which are 1,2-bisphosphates; 2,3-bisphosphates; 3,4-bisphosphates; 4,5-bisphosphates, 5,6-bisphosphates and so on. A 1,3 spatial relationship of the at least two phosphate groups includes embodiments which are 1,3-bisphosphates; 2,4-bisphosphates; 3,5-bisphosphates; 4,6-bisphosphates; 5,7-bisphosphates and so on. Those of ordinary skill in the art will fully understand the extension of this principle to 1,4; 1,5; and 1,6 spatial relationships of the at least two phosphate groups.

As noted, the phosphorylated polyol comprises one or more hydrophilic groups selected from the group consisting of polyethylene ether moieties, polypropylene ether moieties, polybutylene ether moieties, and combinations of two or more of the foregoing hydrophilic moieties. The effectiveness of the phosphorylated polyol in stabilizing the nanoparticulate metal oxide core (and the nanoparticle composition as a whole) has been found to depend upon its structure. In various embodiments, the effectiveness of the phosphorylated polyol in stabilizing the nanoparticulate metal oxide core is dependent upon the size of the hydrophilic moiety which may at times herein be described in terms of the group molecular weight of the hydrophilic group. In general, the structure of the phosphorylated polyol may be tailored to be effective in stabilizing a particular nanoparticulate metal oxide core, and the hydrophilic group present in the phosphorylated polyol may have either a relatively low group molecular weight (e.g. less than 100 grams per "mole") or a relatively high group molecular weight (e.g. more than 10,000 grams per "mole"). Those of ordinary skill in the art will understand that because the hydrophilic group comprises one or more of a polyethylene ether moiety, a polypropylene ether moiety, a polybutylene ether moiety, and combinations of two or more of the foregoing hydrophilic moieties, the size and molecular weights of these moieties, at times herein referred to as moiety molecular weight, will contribute to the group molecular weight of the hydrophilic group as a whole. In one embodiment, the hydrophilic group comprises a polyethylene ether moiety having a moiety molecular weight in a range from about 750 daltons to about 20,000 daltons. In an alternate embodiment, the hydrophilic group comprises a polyethylene ether moiety having a moiety molecular weight of about 2000 daltons. In yet another embodiment, the hydrophilic group comprises a polyethylene ether moiety having a moiety molecular weight of less than 20,000 daltons. In yet still another embodiment, the hydrophilic group comprises a polyethylene ether moiety having a moiety molecular weight of less than 2000 daltons. In yet another embodiment, the hydrophilic group comprises a polyethylene ether moiety having a moiety molecular weight of less than 350 daltons. As used herein, "daltons" and "grams per mole" may be used as interchangeable terms which when applied either to the group molecular weight of a hydrophilic group or the moiety molecular weight of a polyethylene ether moiety, polypropylene ether moiety, polybutylene ether moiety, combinations of two or more of the foregoing hydrophilic moieties, and substituted variants of such moieties, and expresses the weight in grams of the that group or moiety present in a mole of the phosphorylated polyol which contains it.

The intended end use of the nanoparticle composition may impact the selection of the hydrophilic groups used in the phosphorylated polyol. For instance, where the nanoparticle compositions are to be used in vivo, particularly in human subjects, it may be desirable to avoid hydrophilic groups containing ionic groups which might bind strongly to tissue components such as proteins. For in vivo use, hydrophilic groups with essentially no net charge, such as polyalkylene ethers are of particular interest. In addition, for use in human subjects, hydrophilic groups that are innocuous and permit the nanoparticle composition to be easily and reproducibly characterized for safety evaluation are particularly desirable. The nanoparticle composition provided by the present invention typically has a zeta potential in a range from about −40 mV and +40 mV.

In one embodiment, the phosphorylated polyol has structure V

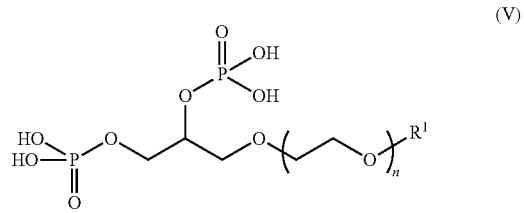

(V)

wherein n is an integer from about 6 to about 150 and $R^1$ is an alkyl group or a hydrogen atom. The phosphorylated 1,2-diol V is illustrated by phosphorylated polyol 10 (Experimental Section Example 5, n=10, $R^1$=methyl) also referred to herein as 1,2BPP440. Phosphorylated 1,2-diol V is further illustrated by phosphorylated polyol 15 (Experimental Section Example 7, n=17, $R^1$=methyl) also referred to herein as 1,2BPP750. In one embodiment, the present invention a phosphorylated 1,2-diol having structure V wherein n is in a range from about 16 to about 150 and $R^1$ is an alkyl group or a hydrogen atom. See, for example, phosphorylated 1,2-diol 20 ((Experimental Section Example 9, n=44, $R^1$=methyl).

In an alternate embodiment, the phosphorylated polyol has structure VI

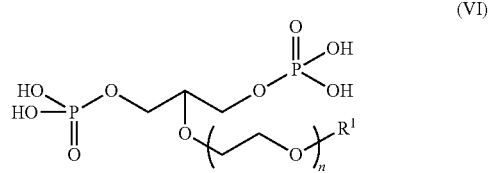

(VI)

wherein n is an integer from about 6 to about 150 and $R^1$ is an alkyl group or a hydrogen atom. The phosphorylated 1,3-diol VI is illustrated by phosphorylated polyol 27 (Experimental Section Example 13, n=7, $R^1$=methyl) also referred to herein as 1,3BPP350. In one embodiment, the present invention a phosphorylated 1,3-diol having structure VI wherein n is in a range from about 16 to about 150 and $R^1$ is an alkyl group or a hydrogen atom. See, for example, phosphorylated 1,3-diol 31 ((Experimental Section Example 15, n=44, $R^1$=methyl) also referred to herein as 1,3BPP2000.

In yet another embodiment, the phosphorylated polyol comprising at least two phosphate groups and one or more hydrophilic groups has structure XVIII

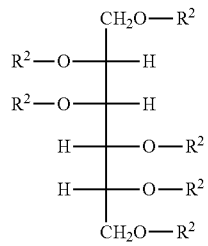

XVIII wherein O—R² is independently at each occurrence a phosphate group, a hydroxy group, or a polyethylene ether moiety.

As used herein in relation to phosphorylated polyols and nanoparticle compositions comprising such phosphorylated polyols or nanoparticle compositions comprising structural units derived from such phosphorylated polyols, the designation "1,2-BPP350" refers to a phosphorylated polyol comprising two phosphate groups configured in a 1,2 spatial relationship and a polyethylene ether moiety having a moiety molecular weight of 350 daltons. Similarly, the designation "1,2-BPP440" refers to a phosphorylated polyol comprising two phosphate groups configured in a 1,2 spatial relationship and a polyethylene ether moiety having moiety molecular weight of 440 daltons.

As used herein the designation P2P4Man refers to a phosphorylated mannitol comprising approximately two phosphate groups per mannitol residue and approximately four hydrophilic groups comprising polyethylene ether moieties. Structure 23 in the Experimental Section illustrates such a mannitol-based phosphorylated polyol.

Nanoparticle compositions provided by the present invention are illustrated by structures VII-XVI below wherein the disc-shaped component labeled Fe₃O₄ represents a nanoparticulate metal oxide core and the associated phosphorylated polyol structure represents one or more phosphorylated polyols bound to the nanoparticulate metal oxide core. Structures VII-XVI are not meant to suggest a 1:1 stoichiometry between the nanoparticulate metal oxide core and the phosphorylated polyol, but rather to identify the nanoparticle composition as comprising a the nanoparticulate metal oxide care and at least one phosphorylated polyol. As noted, the phosphorylated polyol may be in a fully protonated form as shown in structures VII-XVI, or in an ionized form. (See Forms II and III herein). Typically, a plurality of phosphorylated polyols will be associated with the surface of a given nanoparticulate metal oxide core particle. In some embodiments, the phosphorylated polyol is bound to the nanoparticulate metal oxide core via hydrogen bonds. In some embodiments, the phosphorylated polyol is bound to the nanoparticulate metal oxide core via at least one covalent bond. In other embodiments, the phosphorylated polyol may be bound to the nanoparticulate metal oxide core via ionic bonds. In certain embodiments, the precise nature of the chemistry through which the phosphorylated polyol is bound to the nanoparticulate metal oxide core may not be well understood. Notwithstanding such uncertainty, basic structure-activity principles for a variety of such nanoparticle compositions provided by the present invention may be discerned through experimentation, and such experimentally determined structure-activity principles are disclosed herein.

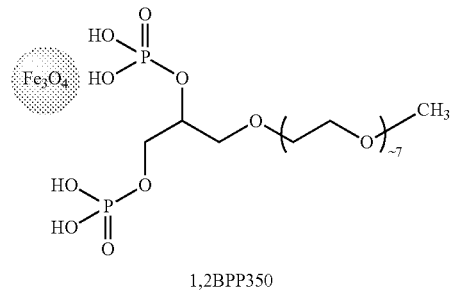

VII 1,2BPP350

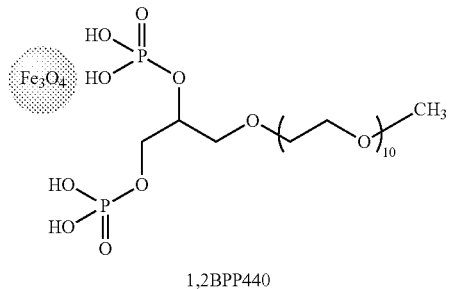

VIII 1,2BPP440

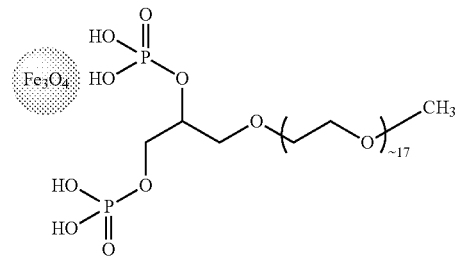

IX 1,2BPP750

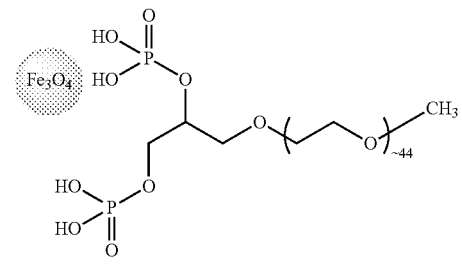

X 1,2BPP2000

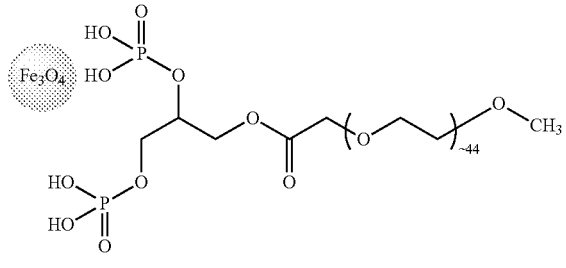

XI 1,2BPP2000Ester

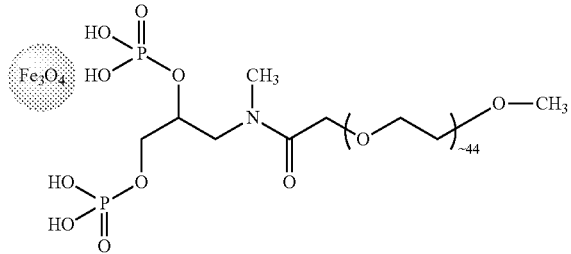

1,2BPP2000Amide

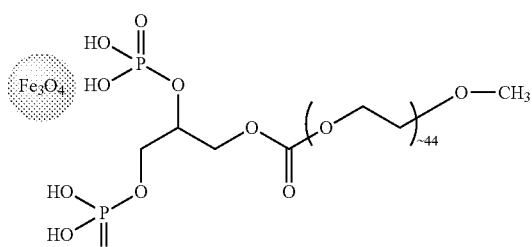

1,2BPP2000Carbonate

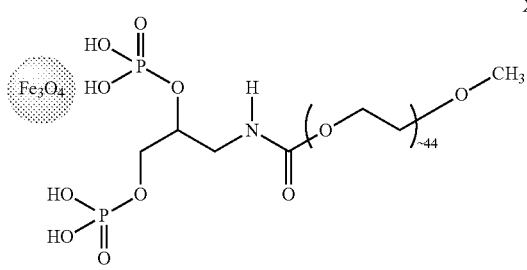

1,2BPP2000Carbamate

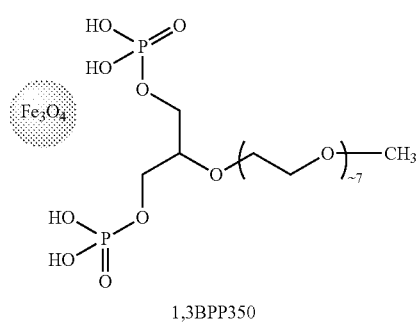

1,3BPP350

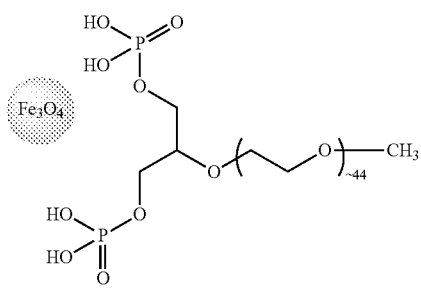

1,3BPP2000

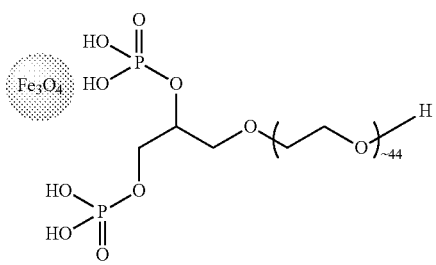

1,2BPP2000-OH

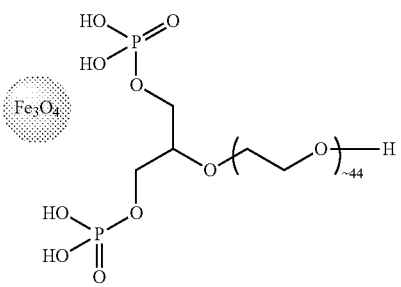

1,3BPP2000-OH

As illustrated in structures XI, XII, XIII and XIV the phosphorylated polyol component of the nanoparticle composition may, in certain embodiments, comprise a hydrophilic group containing groups in addition to the ether linkages (—O—) found in polyalkylene ether moieties. Thus, a wide variety of functional groups in addition to ether groups may be present in the phosphorylated polyol, for example ester groups, amine groups, amide groups, carbamate groups, urea groups, carbonate groups, thioether groups, selenoether groups, siloxane groups, sulfinyl groups, sulfonyl groups, and combinations of two or more of the foregoing groups. As will be appreciated by those of ordinary skill in the art, such functional groups may be constituents of the hydrophilic group itself or may constitute a part of the phosphorylated polyol which is not identified as the hydrophilic group. The intended end use of the nanoparticle compositions may impact the choice of such functional groups.

As noted, the nanoparticle composition provided by the present invention typically comprises a transition metal oxide core and a shell comprised of a phosphorylated polyol. In the product nanoparticle composition the ratio of the shell to the core may be determined by elemental analysis. From knowledge of the chemical make up of the metal oxide nanoparticles and their average size before treatment with the phosphorylated polyol, a calculation can be made of the amount of phosphorylated polyol per nanoparticulate metal oxide core particle. In one embodiment, the present invention provides a nanoparticle composition comprising a nanoparticulate iron oxide core and a phosphorylated polyol shell wherein the molar ratio of phosphorylated polyol to iron is in a range from about 0.01 to about 0.25. In an alternate embodiment, the present invention provides a nanoparticle composition comprising a nanoparticulate tantalum oxide core and a phosphorylated polyol shell wherein the molar ratio of phosphorylated polyol to tantalum is in a range from about 1 to about 2. In one embodiment, the present invention provides a nanoparticle composition comprising a nanoparticulate SPIO core, and a phosphorylated polyol shell wherein the molar ratio of the phosphorylated polyol to the iron in the nanoparticulate SPIO core is in a range from about 0.01 to 0.25.

One aspect of the invention relates to methods for making the nanoparticle compositions. In general, the method for making a nanoparticle composition comprises contacting a nanoparticulate metal oxide core with a phosphorylated polyol shell composition of the present invention. The Experimental Section of this disclosure provides extensive guidance on the preparation of the nanoparticle composition provided by the present invention. Typically, the contacting is carried out in a mixture comprising at least one organic solvent and water.

In one embodiment, the method comprises providing a nanoparticulate metal oxide core, and disposing a phosphorylated polyol shell on the core. In one or more embodiments, the step of providing a nanoparticulate metal oxide core comprises providing a first precursor material comprising a transition metal, the first precursor material being susceptible to nanoparticulate metal oxide formation. In one embodiment, the first precursor material may react with an organic acid to generate the nanoparticulate metal oxide core. The term "reacts" includes mixing two or more reactants under conditions which allow them to interact. In an alternate embodiment, the first precursor material may decompose to generate the nanoparticulate metal oxide core. In another embodiment, the first precursor material may hydrolyze to generate the nanoparticulate metal oxide core. Thus, in one embodiment nanoparticulate metal oxide core is provided by hydrolysis of a metal alkoxide in the presence of an organic acid. For example, nanoparticulate tantalum oxide tantalum may be prepared by hydrolysis of tantalum ethoxide. The organic acid may be, for instance, a carboxylic acid such as isobutyric acid. The hydrolysis reaction may be carried out in the presence of an alcohol solvent, such as 1-propanol or methanol. Methods for the preparation of nanoparticulate metal oxide particles are well known in the art and any suitable method for making a nanoparticle core of an appropriate material may be suitable for use in this method.

The Experimental Section of this disclosure provides detailed guidance on protocols for disposing a phosphorylated polyol shell on the nanoparticulate metal oxide core. In one or more embodiments, disposing the shell on the core comprises providing a second precursor material comprising a phosphorylated polyol or a precursor thereto. In some embodiments, the precursor to the phosphorylated polyol may undergo a hydrolysis reaction in the presence of the nanoparticulate metal oxide core and thereafter attach to the surface of the nanoparticulate metal oxide core. In an alternate embodiment, the precursor to the phosphorylated polyol can be attached to the surface of the nanoparticulate metal oxide core and thereafter hydrolyzed.

As noted, the nanoparticle compositions provided by the present invention may be used as contrast agents for diagnostic imaging. In such an application, these nanoparticle compositions are administered to a subject, in some embodiments a mammalian subject, and then the subject is thereafter subjected to imaging. The nanoparticle compositions provided by the present invention may be particularly useful in MR and X-ray imaging though they may also find utility as contrast agents in ultrasound or radioactive tracer imaging. In addition, the nanoparticle compositions provided by the present invention may be useful in other areas such as cell culture infusion.

In one embodiment, the present invention provides a diagnostic agent composition suitable for injection into a mammalian subject, and the diagnostic agent composition comprises a nanoparticle composition and a pharmaceutically acceptable carrier or excipient. The nanoparticle composition comprises a nanoparticulate metal oxide and a phosphorylated polyol, the phosphorylated polyol comprising at least two phosphate groups and one or more hydrophilic groups selected from the group consisting of polyethylene ether moieties, polypropylene ether moieties, polybutylene ether moieties, and combinations of two or more of the foregoing hydrophilic moieties. In one embodiment, the excipient is an optional component of the diagnostic agent composition. Suitable excipients are illustrated by, but not limited to, one or more of salts, disintegrators, binders, fillers, and lubricants. In one embodiment, the pharmaceutically acceptable carrier may be substantially water.

Diagnostic agent compositions provided by the present invention may be prepared by contacting a nanoparticle composition of the present invention with a pharmaceutically acceptable carrier and/or excipient.

In yet another embodiment, the present invention provides a method of performing diagnostic imaging, the method comprising (a) administering a diagnostic agent composition of the present invention to a subject in a pharmaceutically acceptable carrier or excipient; and (b) subjecting the subject to diagnostic imaging, wherein the diagnostic agent composition acts as a contrast agent. The diagnostic agent composition may be administered by injection, inhalation, ingestion, parenteral injection, or intravenous injection.

When used in diagnostic imaging, particularly of mammalian subjects and more particularly of human subjects, the diagnostic agent compositions provided by the present invention, are typically administered as a suspension in a pharmaceutically acceptable carrier which may (but is not required to) comprise one or more excipients. If the administration is to be by injection, particularly parenteral injection, the carrier is typically an aqueous medium that has been rendered isotonic by the addition of about 150 mM of NaCl, 5% dextrose or combinations thereof. It typically also has an appropriate (physiological) pH of between about 7.3 and 7.4. The administration may be intravascular (IM), subcutaneous (SQ) or most commonly intravenous (IV). However, the administration may also be via implantation of a depot that then slowly releases the nanoparticles into the subject's blood or tissue. Alternatively, the administration may be by ingestion for imaging of the GI tract or by inhalation for imaging of the lungs and airways.

The administration to human subjects, particularly intravenous administration, requires that the diagnostic agent composition be non-toxic in the amounts used and free of any infective agents such as bacteria and viruses and also free of any pyrogens. Thus, the nanoparticle composition present in the diagnostic agent composition should be stable to the necessary purification procedures and not suffer degradation in their hydrophilicity or change in the size of the constituent nanoparticles.

In one embodiment, the present invention provides a diagnostic agent composition which may be delivered to the site of administration as a stable aqueous colloidal suspension with the proper osmolality and pH, as a concentrated aqueous colloidal suspension suitable for dilution prior to administration to a subject. In an alternate embodiment, the present invention provides a diagnostic agent composition as a powder, such as obtained by lyophilization, suitable for reconstitution.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

EXPERIMENTAL SECTION

Example 1

Synthesis of a Nanoparticulate Metal Oxide Core (SPIO)

To a 20 mL solution of anhydrous benzyl alcohol, 0.706 g of iron (III) acetylacetonate (2 mmol) and 0.414 g of 1-phenyl-1,2-ethanediol (3 mmol) were added under stirring condition and the resulting mixture was heated at 170° C. for 4 hrs. The reaction mixture was cooled to ambient temperature to form a SPIO core solution containing 5.6 mg of Fe/mL.

Example 2

Synthesis of 1,2 Bis phosphate PEG 350 (1,2BPP350) (5)

A stirred solution of PEG350 monomethyl ether (35 g, 100 mmol) and triethylamine (20.2 g, 200 mmol) in methylene chloride (200 mL) was cooled to 0° C., and methane sulfonyl chloride (17.1 g, 150 mmol) was added drop-wise. The reaction was then allowed to warm to room temperature and was stirred for an additional 3 h. A solution of saturated aqueous ammonium chloride (100 mL) was then added and the layers were separated. The organic layer was washed with saturated aqueous ammonium chloride (3×100 mL), saturated aqueous sodium bicarbonate solution (1×100 mL), and finally with a saturated aqueous sodium chloride solution (1×100 mL). The organic solution was then dried over anhydrous sodium sulfate, filtered, and the solvent removed under reduced pressure to yield 48 g of compound 1 as an oil.

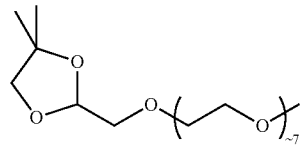

(1)

Freshly powdered potassium hydroxide (2.98 g, 53.1 mmol) was added to anhydrous DMSO (100 mL), and the mixture was stirred for 1 hour under an inert atmosphere. 1,2-isopropylideneglycerol (2.81 g, 21.3 mmol) was then added, followed by a drop-wise addition of PEG350 mesylate compound 1 (9.1 g, 21.3 mmol) in 50 ml of anhydrous DMSO. The mixture was then heated to 40° C. and stirred for 18 hours under inert atmosphere. The reaction mixture was then cooled to ambient temperature, diluted with water (200 mL), and extracted with methylene chloride (4×200 mL). The combined organic layers were then washed with water (2×200 mL) and concentrated under reduced pressure yielding compound 2 as a yellow oil. $^1$H NMR (400 MHz, CDCl$_3$, δ): 4.3 (1H, m), 4.05-4.2 (2H, m), 3.5-3.75 (32H, m), 3.4 (3H, s), 1.43 (3H, s), 1.37 (3H, s).

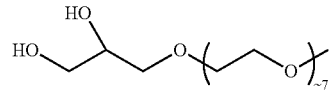

(2)

1N HCl in methanol (50 mL) was added to a stirred solution of 2 (8.8 g, 21.4 mmol) in methanol (50 mL), and the reaction was stirred for 18 h at ambient temperature. The mixture was then concentrated under reduced pressure and dried under high vacuum to yield 8 g of compound 3 as an oil. $^1$H NMR (400 MHz, CDCl$_3$, δ): 3.95-4.0 (2H, bs), 3.9 (1H, m), 3.55-3.8 (32H, s), 3.4 (3H, s).

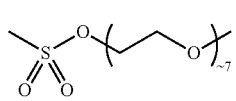

(3)

Tetrazole (0.45M in acetonitrile, 32.4 mmol) was added to a solution of dibenzyl N,N-diisopropylphosphoramidite (11.19 g, 32.4 mmol) in methylene chloride (300 mL), and the mixture was stirred at ambient temperature for 30 min. Diol compound 3 (3.0 g, 8.1 mmol) was then added and the mixture was stirred for 18 h at ambient temperature. The reaction was then cooled to −78° C. and m-chloroperoxybenzoic acid (77%) (59 g, 32.4 mmol) was added as a single portion. The reaction mixture was then stirred at −78° C. for 10 minutes, allowed to warm to room temperature and then stirred for an additional 4 h. A 10% (w/v) aqueous solution of sodium sulfite (100 mL) was then added and the layers were separated. The aqueous layer was back extracted with methylene chloride (100 mL) and the combined organic extracts were evaporated under reduced pressure. The resulting yellow oil was purified using column chromatography (hexanes:ethyl acetate) followed by a solvent change (methylene chloride:methanol) yielding 4.58 g of compound 4. $^1$H NMR (400 MHz, CDCl$_3$, δ): 7.28-7.35 (20H, m), 5.0-5.1 (8H, m), 4.7 (1H, m), 4.1-4.25 (2H, m), 3.55-3.8 (32H, m), 3.4 (3H, s).

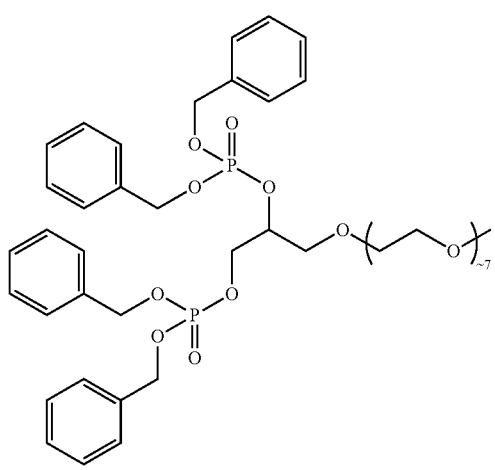

(4)

Palladium on carbon (10%, 3 g) was added to a solution of compound 4 (4.58 g, 5.14 mmol) in ethanol (100 mL) and the mixture was stirred at ambient temperature under an H₂ atmosphere for 2 days. The reaction mixture was then filtered through celite and the filter cake was washed with ethanol (2×50 mL). The filtrate was evaporated under reduced pressure yielding 6 g of compound 5 as a waxy solid. $^1$H NMR (400 MHz, D₂O, δ): 4.38 (1H, bs), 3.9-4.0 (2H, m), 3.5-3.7 (32H, m), 3.27 (3H, s).

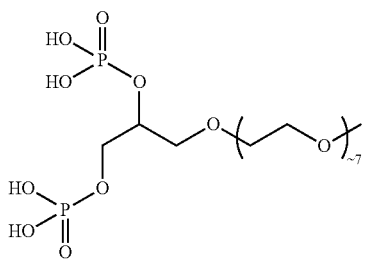

(5)

Example 3

Synthesis of Nanoparticle Composition (VII) (1,2BPP350 SPIO)

PEG350 Bisphosphate compound 5 (1.06 g, 2 mmol) was dissolved in 200 mM aqueous sodium hydroxide solution (20 mL). THF (20 mL) was then added, and the pH of the solution was adjusted to 8 by drop-wise addition of 3M sodium hydroxide. A solution of SPIO cores in benzyl alcohol (10 mL of the 5.6 mg Fe/mL solution) was then added, and the solution was stirred overnight at 50° C. The reaction was then cooled to ambient temperature and diluted with hexanes (50 mL). The layers were separated and the aqueous layer was purified by tangential flow filtration (50K MWCO membrane washed against 4 L of water) to provide a stable suspension of the nanoparticle composition VII. The final particles had a hydrodynamic diameter of 9 nM as measured in a 150 mM sodium chloride solution by dynamic light scattering. The size of the particles did not change after 2 days in the 150 mM sodium chloride solution incubated at 40° C.

Example 4

Synthesis of 1,2BPP350 Tantalum Oxide

Water (0.11 mL) was added to a stirred solution of compound 5 (3.92 g, 7.4 mmol) dissolved in anhydrous methanol (75 mL), and the solution was stirred for 20 minutes. Tantalum ethoxide (1.5 g, 3.69 mmol) was then added drop-wise, the mixture was stirred at ambient temperature for 1 h, and then heated at 50° C. for 18 h. The reaction was then cooled to ambient temperature and diluted with water (250 mL). The pH was adjusted to ~8 by the addition of ammonium hydroxide, the solution was concentrated until the methanol was fully evaporated, and the remaining aqueous solution was passed through a 100 nm filter. The particles were purified using dialysis (3.5K MWCO PES membrane washed against 1 L of water with 4 exchanges). The retained solution was then passed through a 100 nm filter yielding particles having a hydrodynamic size of 4.7 nM as measured in water by dynamic light scattering.

Example 5

Synthesis of 1,2BPP440 (10)

A solution of monodisperse decaethylene glycol monomethyl ether (Biomatrik; Zhejiang, China) (10 g, 21 mmol) and triethylamine (3.85 g, 38 mmol) in methylene chloride (200 mL) was cooled to -30° C., and methane sulfonyl chloride (3.64 g, 31.7 mmol) was added drop-wise. The reaction was allowed to warm to 0° C. over 3 h. Saturated aqueous ammonium chloride (100 mL) was then added and the layers were separated. The aqueous layer was back extracted with methylene chloride (50 mL), the combined organics washed with a saturated aqueous sodium bicarbonate solution (1×100 mL), dried over magnesium sulfate, filtered, and the solvent removed under reduced pressure to yield 12 g of compound 6 as an oil.

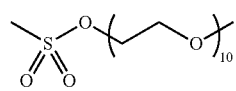

(6)

Freshly powdered potassium hydroxide (3.04 g, 54.3 mmol) was added to anhydrous DMSO (200 mL), and the mixture was stirred for 1.5 hours under an inert atmosphere. A solution of 1,2-isopropylideneglycerol (2.87 g, 21.7 mmol) and PEG440 mesylate compound 6 (12.0 g, 21.7 mmol) in 20 ml of anhydrous DMSO was added, and the mixture was stirred for 18 hours at 40° C. under inert atmosphere. The reaction mixture was then cooled to ambient temperature, diluted with water (250 mL) and extracted with methylene chloride (2×500 mL). The combined organic layers were then washed with water (1×500 mL) and concentrated under reduced pressure yielding compound 7 as a light yellow oil. $^1$H NMR (400 MHz, CDCl₃, δ): 4.3 (1H, m), 4.05-4.1 (1H, m), 3.7-3.8 (2H, m), 3.6-3.7 (39H, m), 3.5-3.6 (4H, m), 3.4 (3H, s), 1.4 (6H, d).

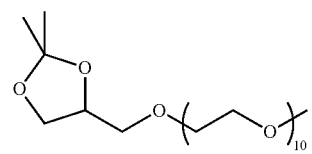

(7)

1N HCl in methanol (50 mL) was added to a stirred solution of 7 (9.17 g, 15.6 mmol) in methanol (50 mL). The reaction was stirred for 18 h at ambient temperature, then concentrated under reduced pressure and dried under high vacuum to yield 8.8 g of compound 8 as an oil. $^1$H NMR (400 MHz, CDCl₃, δ): 3.9 (1H, m), 3.65-3.8 (40H, s), 3.55-3.65 (4H, m), 3.4 (3H, s).

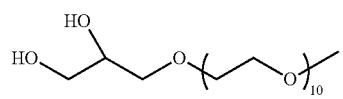

(8)

Tetrazole (0.45M in acetonitrile, 22 mmol) was added to a solution of dibenzyl N,N-diisopropylphosphoramidite (7.62 g, 22 mmol) in methylene chloride (300 mL), and the mixture was stirred at ambient temperature for 30 min. Diol compound 8 (3.0 g, 5.5 mmol) was then added, the mixture was stirred for 18 h at ambient temperature. The reaction was then cooled to −78° C. and m-chloroperoxybenzoic acid (77%) (3.81 g, 22 mmol) was added as a single portion. The reaction mixture was then stirred at −78° C. for 10 minutes, allowed to warm to room temperature and then stirred for an additional 4 h. A 10% (w/v) aqueous solution of sodium sulfite (100 mL) was then added and the layers were separated. The aqueous layer was back extracted with methylene chloride (100 mL) and the combined organic extracts were evaporated under reduced pressure. The resulting oil was purified using column chromatography (hexanes:ethyl acetate) followed by a solvent change (methylene chloride:methanol) yielding 1.56 g of compound 9. $^1$H NMR (400 MHz, CDCl$_3$, δ): 7.3-7.4 (20H, m), 5.0-5.1 (8H, m), 4.7 (1H, m), 4.1-4.25 (2H, m), 3.55-3.7 (42H, m), 3.4 (3H, s).

(9)

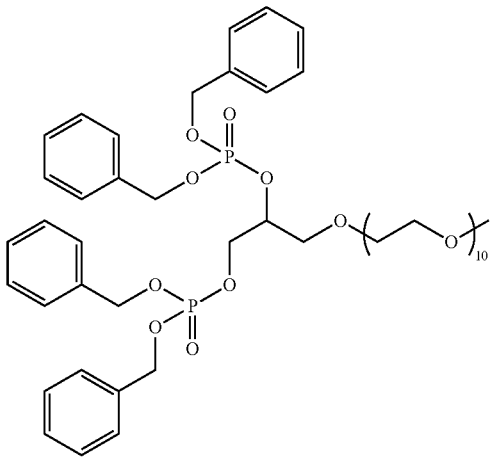

Palladium on carbon (10%) (0.25 g) was added to a stirred solution of compound 9 (1.56 g, 1.46 mmol) in ethanol (100 mL), and the mixture was stirred at ambient temperature under an H$_2$ atmosphere for 2 days. The reaction mixture was then filtered through celite and the filter cake washed with ethanol (2×50 mL). The filtrate was evaporated under reduced pressure yielding 1.03 g of compound 10 as a clear oil. $^1$H NMR (400 MHz, D$_2$O, δ): 4.395 (1H, m), 3.9-4.0 (2H, m), 3.5-3.65 (42H, m), 3.25 (3H, s).

(10)

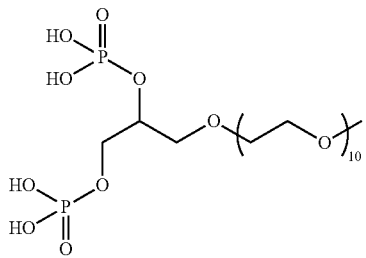

Example 6

Synthesis of Nanoparticle Composition (VIII)
(1,2BPP440 SPIO)

1M aqueous sodium hydroxide (3 mL) was added to a stirred solution of compound 10 (0.71 g, 2 mmol) dissolved in THF (20 mL) and water (15 mL). A solution of SPIO cores in benzyl alcohol (10 mL of the 5.6 mg Fe/mL solution) was then added, and the mixture was stirred overnight at 50° C. The reaction was then cooled to ambient temperature and diluted with hexanes (2×50 mL). The layers were separated and the aqueous layer was then purified by tangential flow filtration (30K MWCO membrane washed against 4 L of water) to provide a stable suspension of the nanoparticle composition VIII. The final particles had a hydrodynamic diameter of 10.3 nM as measured in water by dynamic light scattering. The size of the particles did not change after 2 days in 150 mM sodium chloride solution incubated at 40° C.

Example 7

Synthesis of a 1,2BPP750 (15)

A solution of PEG750 monomethyl ether (75 g, 100 mmol) and triethylamine (30.3 g, 300 mmol) in methylene chloride (700 mL) was cooled to 0° C., and methane sulfonyl chloride (22.8 g, 200 mmol) was added drop-wise. The resulting reaction was allowed to warm to room temperature and then stirred for an additional 3 h. A solution of saturated aqueous ammonium chloride (200 mL) was then added and the layers were separated. The organic layer was washed with saturated aqueous ammonium chloride (4×200 mL), saturated aqueous sodium bicarbonate solution (1×200 mL), and finally with a saturated aqueous sodium chloride solution (1×200 mL). The organic solution was then dried over anhydrous sodium sulfate, filtered, and the solvent removed under reduced pressure to yield 84 g of compound 11 as an oil. $^1$H NMR (400 MHz, CDCl$_3$, δ): 4.36 (2H, m), 3.75 (2H, m), 3.62 (64H, br. s), 3.55 (2H, m), 3.35 (3H, 3), 3.07 (3H, s).

(11)

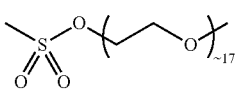

Freshly powdered potassium hydroxide (12.75 g, 225 mmol) was added to anhydrous DMSO (150 mL), and the mixture was stirred for 30 minutes under an inert atmosphere. 1,2-isopropylideneglycerol (26.4 g, 200 mmol) was then added, followed by a drop-wise addition of PEG mesylate compound 11 (84 g, 100 mmol) in 500 ml of anhydrous DMSO. The mixture was stirred for three days under inert atmosphere. A mixture of 80% aqueous sodium chloride (700 mL) and methylene chloride (500 mL) was then added, the layers were separated, and the aqueous layer was back-extracted with methylene chloride (4×300 mL). The combined organic layers were then washed with saturated sodium chloride (1×500 mL), dried over anhydrous sodium sulfate, and filtered. The solvent was removed under reduced pressure, and the remaining DMSO was distilled off under high vacuum. The material was then dissolved in warm THF (200 mL) and heptane (75 mL), a small amount of solid was filtered off, and the filtrate was allowed to crystallize overnight at 5° C. At this time, cold heptane (200 mL) was added, the solid was collected via cold filtration. Residual 1,2-isopropylideneglycerol was removed by dissolving the material in water (700 mL) and washing with heptane (5×150 mL), yielding product compound 12 in aqueous solution. The solvent was removed from a small aliquot of the aqueous solution, yielding solid compound 12. $^1$H NMR (400 MHz, CDCl$_3$, δ): 4.15 (1H, m), 3.92 (1H, m), 3.3-3.7 (68H, m), 3.25 (3H, s), 1.25 (6H, d).

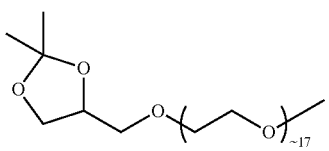
(12)

The resulting aqueous solution of compound 12 (700 mL) was mixed with 3N HCl (100 mL), and stirred overnight. The majority of the water was then stripped off via rotary evaporation, and the remaining material was suspended in methylene chloride (600 mL). Solid anhydrous sodium carbonate (50 g) was then added cautiously, and the mixture stirred for 1 hour. The solid was filtered off, and the solvent removed via rotary evaporation. Toluene (300 mL) was then added and the solution was refluxed for 2 hours with a Dean Stark trap to remove any remaining water. The solution was then cooled to room temperature, the toluene was stripped off by rotary evaporation, and the remaining material was dried under hi vacuum to yield 72 g of compound 13 as an oily solid. $^1$H NMR (400 MHz, CDCl$_3$, δ): 3.78 (2H, m), 3.45-3.7 (68H, m), 3.35 (3H, s).

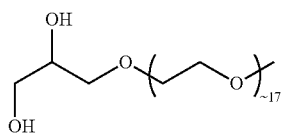
(13)

Tetrazole (0.45M in acetonitrile, 72.8 mmol) was added to a solution of dibenzyl N,N-diisopropylphosphoramidite (25.1 g, 72.8 mmol) in methylene chloride (200 mL), and the mixture was stirred at ambient temperature for 30 min. Diol compound 13 was then added (15 g, 18.2 mmol) and the resulting mixture was stirred for 18 h at 40° C. The reaction was then cooled to −35° C., and m-chloroperoxybenzoic acid (77%) (12.6 g, 72.8 mmol) was added as a single portion. The reaction was then stirred at −35° C. for 5 min, allowed to warm to room temperature, and then stirred for an additional 4 h. A 10% (w/v) aqueous solution of sodium sulfite (100 mL) was then added, the reaction was stirred for 30 min, the layers were separated, and the organic layer evaporated under reduced pressure. The resulting yellow oil was purified using column chromatography (hexanes:ethyl acetate) followed by a solvent change (methylene chloride:methanol) yielding 8 g of compound 14 as a clear oil. $^1$H NMR (400 MHz, CDCl$_3$, δ): 7.3-7.4 (20H, m), 5.0-5.1 (8H, m), 4.65 (1H, m), 4.1-4.25 (2H, m), 3.55-3.8 (70H, m), 3.4 (3H, s).

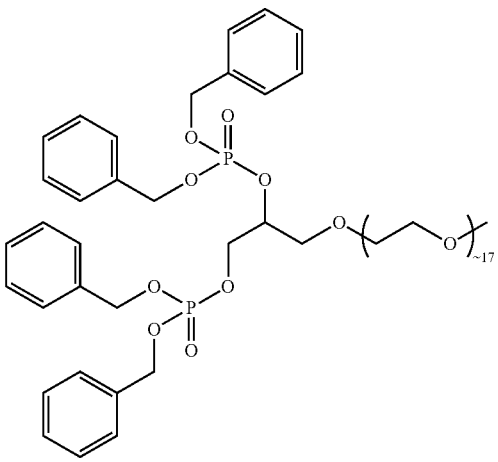
(14)

Palladium on carbon (10%) (0.5 g) was added to a stirred solution of compound 14 (8 g, 5.8 mmol) in ethanol (100 mL), and the mixture was stirred at ambient temperature under an H$_2$ atmosphere for 2 days. The reaction mixture was then filtered through celite and the filter cake was washed with ethanol (2×50 mL). The filtrate was evaporated under reduced pressure yielding 6 g of compound 15 as a waxy solid. $^1$H NMR (400 MHz, CDCl$_3$, δ): 4.75 (1H, bs), 4.1-4.3 (2H, m), 3.55-3.8 (70H, m), 3.4 (3H, s).

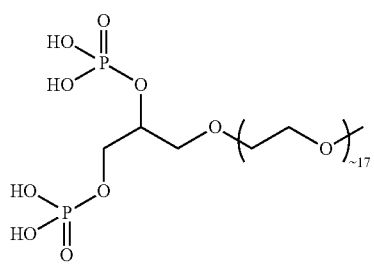
(15)

Example 8

Synthesis of Nanoparticle Composition (IX) (1,2BPP750 SPIO)

1M aqueous sodium hydroxide solution (0.6 mL) was added to a stirred solution of PEG750 bisphosphate compound 15 (0.203 g, 0.2 mmol) dissolved in THF (4 mL) and water (2.5 mL). A solution of SPIO cores in benzyl alcohol (4 mL of a 2.8 mg Fe/mL solution) was then added, and the solution was stirred overnight at 50° C. The reaction was then cooled to ambient temperature and diluted with hexanes (10 mL). The layers were separated and the aqueous layer was then purified using centrifuge filters (30K MWCO washed against water) to provide a stable suspension of the nanoparticle composition IX. The final particles had a hydrodynamic diameter of 13 nM as measured in a 150 mM sodium chloride solution by dynamic light scattering. The size of the particles did not change after 2 days in 150 mM sodium chloride solution incubated at 40° C. The material could be sterilized by autoclave (121° C., 15 minutes, 5% mannitol formulation) with no sign of aggregation or change in particle size.

Example 9

Synthesis of a 1,2BPP2000 (20)

A solution of PEG1900 monomethyl ether (95 g, 50 mmol) and triethylamine (20.2 g, 200 mmol) in methylene chloride (700 mL) was cooled to 0° C., and methane sulfonyl chloride (17.1 g, 150 mmol) was added drop-wise. The resulting reaction was allowed to warm to room temperature and then stirred for an additional 18 h. A solution of saturated aqueous ammonium chloride (200 mL) was then added and the layers were separated. The organic layer was washed with saturated aqueous ammonium chloride (4×200 mL), saturated aqueous sodium bicarbonate solution (1×200 mL), and finally with a saturated aqueous sodium chloride solution (1×200 mL). The organic solution was then dried over anhydrous sodium sulfate, filtered, and the solvent removed under reduced pressure, yielding 100 g of compound 16 as a white solid. $^1$H NMR (400 MHz, CDCl$_3$, δ): 4.38 (2H, m), 3.75 (2H, m), 3.62 (176H, br. s), 3.55 (2H, m), 3.38 (3H, 3), 3.10 (3H, s).

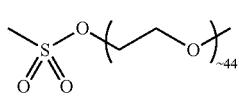

(16)

Freshly powdered potassium hydroxide (11.2 g, 200 mmol) was added to anhydrous DMSO (150 mL), and the mixture was stirred for 30 minutes under an inert atmosphere. 1,2-isopropylideneglycerol (26.4 g, 200 mmol) was then added, followed by a drop-wise addition of PEG2000 mesylate compound 16 (100 g, 50 mmol) in 500 ml of anhydrous DMSO. The mixture was then stirred for three days under inert atmosphere. 80% aqueous sodium chloride (700 mL) and methylene chloride (500 mL) were then added, the layers were separated, and the aqueous layer was back-extracted with methylene chloride (4×300 mL). The combined organic solution was then washed with saturated sodium chloride (1×500 mL), dried over anhydrous sodium sulfate, and filtered. The solvent was removed under reduced pressure, and the remaining DMSO was distilled off under high vacuum. The material was then dissolved in hot THF (300 mL) and heptane (100 mL), a small amount of solid was filtered off, and the filtrate was allowed to crystallize overnight at 5° C. Cold heptane (200 mL) was then added, and the solid was collected via cold filtration. The solid was recrystallized a second time from comparable amounts of solvent, and the product was dried yielding 86 g of compound 17 as a solid. $^1$H NMR (400 MHz, CDCl$_3$, δ): 4.25 (1H, m), 4.00 (1H, m), 3.4-3.8 (172H, m), 3.33 (3H, s), 1.35 (6H, d)

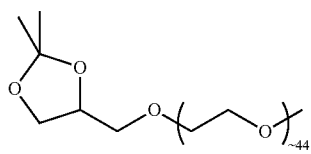

(17)

3N HCl (100 mL) was added to a stirred solution of compound 17 (86 gm) in water (600 mL), and the mixture was stirred overnight. The majority of the water was then stripped off via rotary evaporation, and the remaining material was suspended in methylene chloride (600 mL). Solid anhydrous sodium carbonate (50 g) was then cautiously added, and the mixture stirred for 1 hour. The solid was then filtered off, and the solvent was removed from the filtrate via rotary evaporation. Toluene (300 mL) was then added and the mixture was refluxed for 2 hours with a Dean Stark trap to collect any remaining water. The mixture was then cooled to room temperature, the toluene was removed under reduced pressure, and the remaining material was dried under hi vacuum, yielding 75 g of compound 18 as a solid. $^1$H NMR (400 MHz, CDCl$_3$, δ): 3.78 (2H, m), 3.45-3.7 (185H, m), 3.30 (3H, s).

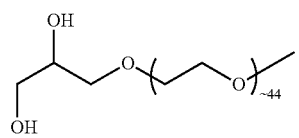

(18)

Tetrazole (0.45M in acetonitrile, 40.5 mmol) was added to a solution of dibenzyl N,N-diisopropylphosphoramidite (14 g, 40.5 mmol) in methylene chloride (200 mL), and the mixture was stirred at ambient temperature for 30 min. Diol compound 18 was added (20 g, 10.1 mmol) and the resulting mixture was stirred for 2d at 40° C. The reaction was then cooled to −35° C., and m-chloroperoxybenzoic acid (77%) (6.98 g, 40.5 mmol) was added as a single portion. The reaction was stirred at −35° C. for 5 min, then allowed to warm to room temperature and stir for an additional 4 h. A 10% (w/v) aqueous solution of sodium sulfite (100 mL) was then added, the reaction was stirred for 30 min, the layers separated, and the organic layer was evaporated under reduced pressure. The resulting yellow oil was purified using column chromatography (hexanes:ethyl acetate) followed by a solvent change (methylene chloride:methanol) yielding 15 g of compound 19 as a solid. $^1$H NMR (400 MHz, CDCl$_3$, δ): 7.29-7.35 (20H, m), 5.0-5.1 (8H, m), 4.65 (1H, m), 4.1-4.25 (2H, m), 3.5-3.75 (184H, m), 3.4 (3H, s).

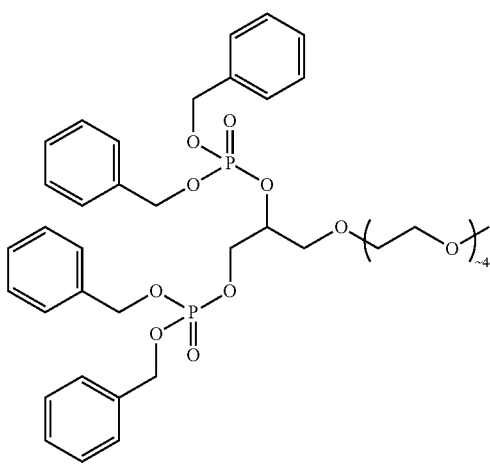

(19)

Palladium on carbon (10%) (0.5 g) was added to a stirred solution of compound 19 (15 g, 5.9 mmol) in ethanol (100 mL), and the mixture was stirred at ambient temperature under an H$_2$ atmosphere for 2d. The reaction mixture was then filtered through celite and the filter cake washed with ethanol (2×50 mL). The filtrate was evaporated under reduced pressure yielding 11.8 g of compound 20 as a waxy solid. $^1$H NMR (400 MHz, CDCl$_3$, δ): 4.75 (1H, bs), 4.2-4.3 (2H, m), 3.55-3.85 (184H, m), 3.4 (3H, s).

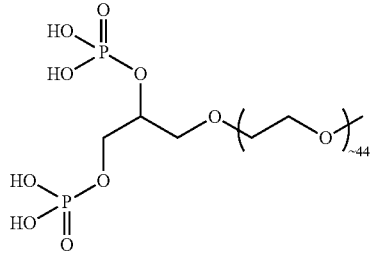

(20)

Example 10

Synthesis of Nanoparticle Composition (X) (1,2BPP2000 SPIO)

A 1M aqueous sodium hydroxide solution (0.6 mL) was added to a stirred solution of PEG2000 bisphosphate compound 20 (0.440 g, 0.2 mmol) in THF (4 mL) and water (2.5 mL). A solution of SPIO cores in benzyl alcohol (4 mL of a 2.8 mg Fe/mL solution) was then added, and the mixture was stirred overnight at 50° C. The reaction was then cooled to ambient temperature and diluted with hexanes (10 mL). The layers were separated and the aqueous layer was then purified via centrifuge filtration (30K MWCO washed against water) to provide a stable suspension of the nanoparticle composition X. The final particles had a hydrodynamic diameter of 16 nM as measured in a 150 mM sodium chloride solution by dynamic light scattering. The size of the particles did not change after 2 days in 150 mM sodium chloride solution incubated at 40° C. The material could be sterilized by autoclave (121° C., 15 minutes) with no sign of aggregation or change in particle size

Example 11

Synthesis of a Mannitol-Based Phosphorylated polyol "P2P4Man" (23)

Freshly powdered potassium hydroxide (0.47 g, 8.4 mmol) in anhydrous DMSO (30 mL) was stirred for 30 minutes under an inert atmosphere. Mannitol (0.182 g, 1 mmol) was then added, followed by PEG440 mesylate compound 6 (2.2 g, 4 mmol). The mixture was stirred for three days under inert atmosphere. 80% saturated aqueous sodium chloride (100 mL) and methylene chloride (100 mL) were then added, the layers were separated, and the aqueous layer was back-extracted with methylene chloride (4×75 mL). The combined organic solution was then washed with saturated sodium chloride (1×100 mL), dried over anhydrous sodium sulfate, and filtered. The filtrate was removed under reduced pressure, and the remaining DMSO was distilled off under high vacuum yielding 2.3 g of compound 21 as a thick oil. $^1$H NMR (400 MHz, CDCl$_3$, δ): 3.5-3.9 (44H, m), 3.39 (3H, s) indicated structure 21 wherein the groups O—R$^2$ are principally hydroxy groups and PEG groups O(CH$_2$CH$_2$O)$_{10}$CH$_3$ and wherein the ratio of hydroxy groups to PEG groups is approximately 2.2 to 3.8.

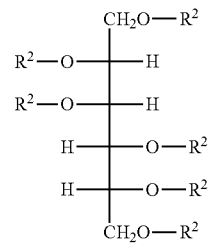

(21)

Tetrazole (0.45M in acetonitrile, 4 mmol) was added to a solution of dibenzyl N,N-diisopropylphosphoramidite (1.38 g, 4 mmol) in methylene chloride (15 mL), and the mixture was stirred at ambient temperature for 30 min. Diol compound 21 (2.3 g, 1 mmol) in 25 mL of methylene chloride was then added, and the resulting mixture was stirred for 3d at ambient temperature under an inert atmosphere. The solution was then cooled to −78° C. and m-chloroperoxybenzoic acid (77%) (0.9 g, 4 mmol) in 10 mL of methylene chloride was added. The reaction was then allowed to warm to room temperature over 2 h with stirring. A 10% (w/v) aqueous solution of sodium sulfite (20 mL) was then added, the reaction was stirred for 30 min, the layers were separated and the aqueous layer was back extracted with methylene chloride (2×20 mL). The combined organic layers were washed with saturated sodium chloride (50 mL), dried over sodium sulfate, filtered and the filtrate evaporated under reduced pressure. The resulting product was purified using column chromatography (hexanes:ethyl acetate) followed by a solvent change (methylene chloride:methanol) yielding 0.7 g of compound 22 the structure of which was confirmed by $^1$H NMR (400 MHz, CDCl$_3$, δ): 7.25 (5.85H, m), 5.0 (2.34H, m), 3.9-3.5 (43H, m), 3.39 (3H, 3). NMR integration indicated that the groups O—R$^2$ were principally dibenzyl phosphate groups (PhCH$_2$O)$_2$PO$_2$ groups and PEG groups O(CH$_2$CH$_2$O)$_{10}$CH$_3$, and that the ratio of phosphorus to PEG was 0.58, with approximately 3.8 PEG groups and approximately 2.2 dibenzyl phosphate groups per molecule.

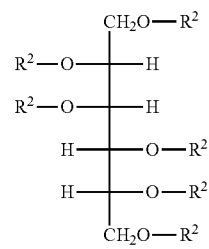

(22)

A solution of compound 22 (0.7 g) in methanol (20 mL) was sparged with nitrogen for 2 minutes, then palladium on carbon (10%) (0.07 g) was added. The reaction was stirred at ambient temperature under an H$_2$ atmosphere for 18 h, after which time TLC analysis indicated that the reaction was complete. The reaction mixture was filtered through celite and the filtrate was evaporated under reduced pressure yielding 0.59 g of compound 23. $^1$H NMR (400 MHz, CDCl$_3$, δ): 4.2-3.5 (44H, m), 3.40 (3H, 3) indicated that the groups O—R$^2$ were principally phosphate groups (HO)$_2$PO$_2$ groups and PEG groups O(CH$_2$CH$_2$O)$_{10}$CH$_3$, with approximately 3.8 PEG groups and approximately 2.2 phosphate groups per molecule.

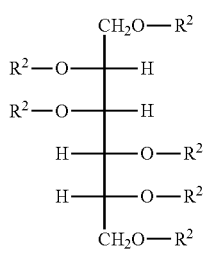

(23)

Example 12

Synthesis of Nanoparticle composition "P2P4Man" SPIO

A reaction vial was charged with water (2 mL), compound 23 (0.214 g) and 5N NaOH (50 uL). The contents were shaken until fully dissolved, yielding a solution with pH=8.0. The mixture was then lyophilized, and the residue was dissolved in THF (10 mL). A solution of SPIO core in benzyl alcohol (2.3 mL, 5.5 mg Fe/mL) was then added, and the solution was capped and stirred overnight at 50° C. Water (6 mL) was then added, the mixture was shaken, and the dark color transferred completely into the aqueous layer. The layers were separated, and the aqueous layer solution was washed with hexane (2 mL) and filtered through a 20 nm filter. The solution was then syringed into a 3500 MW dialysis cassette, and the dialyzed against water (1 L) for 24 hours, changing the dialysis bath water 4 times over the course of the dialysis to provide a stable suspension of nanoparticle composition wherein $R^2$ is. The final particles had a hydrodynamic diameter of 11 nM as measured in a 150 mM sodium chloride solution by dynamic light scattering. The size of the particles did not change after 3 days in the 150 mM sodium chloride solution incubated at 40° C.

Example 13

Synthesis of a 1,3BPP350 (27)

Freshly powdered potassium hydroxide (1.03 g, 18.4 mmol) in anhydrous DMSO was stirred for 1 hour under an inert atmosphere. 1,3-dibenzyloxy-2-propanol (2.0 g, 7.34 mmol) and PEG350 mesylate compound 1 (3.14 g, 7.34 mmol) in 15 ml of anhydrous DMSO were then added, and the mixture was stirred at 40° C. for 18 hours under an inert atmosphere. The reaction mixture was then cooled to ambient temperature, diluted with water (100 mL) and extracted with methylene chloride (2×150 mL). The combined organic layers were then washed with water (2×50 mL) and concentrated under reduced pressure yielding compound 24 as a yellow oil.

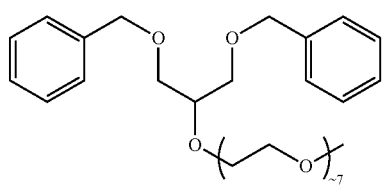

(24)

Palladium on carbon (10%) (0.41 g) was added to a stirred solution of compound 24 (4.5 g, 7.34 mmol) in dry methanol (150 mL), followed by an 88% formic acid solution (5 mL). The mixture was then stirred for 18 h at ambient temperature. The reaction mixture was then filtered through celite and the filter cake washed with methanol (2×50 mL). The filtrate was evaporated under reduced pressure yielding 2.7 g of compound 25 as a clear oil. $^1$H NMR (400 MHz, CDCl$_3$, δ): 3.8-3.9 (2H, m), 3.5-3.8 (32H, m), 3.4 (3H, s).

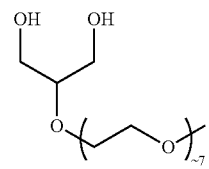

(25)

Tetrazole (0.45M in acetonitrile, 29.4 mmol) was added to a solution of dibenzyl N,N-diisopropylphosphoramidite (10.14 g, 29.4 mmol) in methylene chloride (200 mL), and the mixture was stirred at ambient temperature for 30 min Diol compound 25 (2.7 g, 7.34 mmol) was then added, and the resulting mixture was stirred for 18 h at ambient temperature. The reaction mixture was then cooled to −78° C., and m-chloroperoxybenzoic acid (77%) (5.07 g, 29.4 mmol) was then added as a single portion. The mixture was stirred at −78° C. for 10 minutes, allowed to warm to room temperature and stirred for an additional 4 h. A 10% (w/v) aqueous solution of sodium sulfite (100 mL) was then added and the layers were separated. The aqueous layer was back extracted with methylene chloride (100 mL) and the combined organic extracts were evaporated under reduced pressure. The resulting product was utilized without further purification as yellow oil compound 26. $^1$H NMR (400 MHz, CDCl$_3$, δ): 7.3-7.45 (20H, m), 4.98-5.1 (8H, m), 3.95-4.2 (4H, m), 3.5-3.7 (28H, m), 3.4 (3H, s).

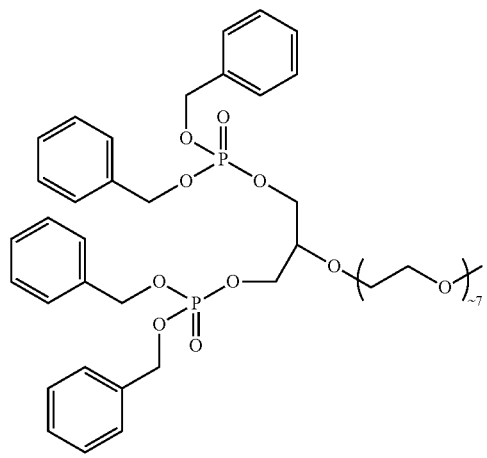

(26)

Palladium hydroxide (0.2 g) was added to a stirred solution of compound 26 (4.18 g, 4.69 mmol) in ethanol (100 mL), and the mixture was stirred at ambient temperature under an H$_2$ atmosphere for 2 days. The reaction mixture was then filtered through celite and the filter cake was washed with ethanol (2×50 mL). The filtrate was then evaporated under reduced pressure yielding 2.5 g of compound 27 as a clear oil. $^1$H NMR (400 MHz, CDCl₃, δ): 3.85-4.0 (3H, m), 3.7-3.8 (2H, m), 3.5-3.65 (28H, m), 3.27 (3H, s).

(27)

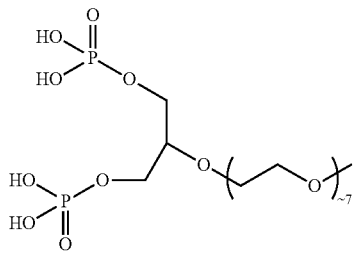

Example 14

Synthesis of Nanoparticle Composition (XVI) (1,3BPP350 SPIO)

THF (1 mL) was added to a stirred solution of compound 27 (0.106 g, 0.2 mmol) in 200 mM aqueous sodium hydroxide solution (1 mL). The pH was then adjusted to 8 by drop-wise addition of a 3M sodium hydroxide solution. A solution of SPIO cores in benzyl alcohol (1 mL of a 5.6 mg Fe/mL solution) was then added, and the mixture was stirred overnight at 50° C. The reaction was then cooled to ambient temperature, the layers separated and the aqueous layer was then purified using dialysis (10K MWCO PES membrane washed against 1 L of water with 4 exchanges). The retained solution was then passed through a 100K MWCO centrifuge membrane to remove any remaining aggregates to provide a stable suspension of nanoparticle composition XVI. The final particles had a hydrodynamic diameter of 9.5 nM as measured in a 150 mM sodium chloride solution by dynamic light scattering.

Example 15

Synthesis of a 1,3BPP2000 (31)

Freshly powdered potassium hydroxide (960 mg, 17.1 mmol) in anhydrous DMSO (10 mL) was stirred for 20 min under an inert atmosphere. 2-Phenyl-1,3-dioxan-5-ol (3.08 gm g, 17.1 mmol) and PEG2000 mesylate compound 16 (8.55 g, 4.27 mmol) in DMSO (80 mL) were then added, and the mixture was stirred for 18 hours at room temperature under an inert atmosphere. A 90% saturated sodium chloride solution (150 mL) and methylene chloride (100 mL) were then added, and the layers were separated. The aqueous layer was extracted with methylene chloride (2×75 mL). The combined organic layers were then washed with saturated sodium chloride (75 mL), dried over anhydrous sodium sulfate, filtered, and then concentrated under reduced pressure yielding compound 28 as a yellow oily solid. Excess DMSO was distilled off under hi vacuum, and the remaining solid was recrystallized from a mixture of hot THF (100 mL) and hot hexane (40 mL). ¹H NMR (400 MHz, CDCl₃, δ): 7.50 (2H, m), 7.38 (3H, m) 5.58 (1H, s), 4.38 (2H, m), 4.05 (2H, m), 3.9-3.5 (176H, m), 3.39 (3H, s).

(28)

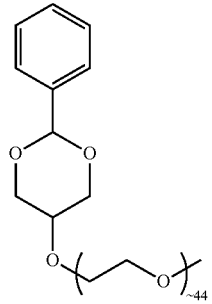

Palladium hydroxide (0.5 g) was added to a stirred solution of compound 28 (4.18 g, 4.69 mmol) in ethanol (100 mL), and the mixture was stirred at ambient temperature under an H₂ atmosphere for 18 hours. The mixture was then filtered through celite and the filter cake was washed with ethanol (2×50 mL). The filtrate was evaporated under reduced pressure yielding 5.0 g of compound 29 as a white sticky solid. ¹H NMR (400 MHz, CDCl₃, δ): 3.85 (3H, m), 3.5-3.75 (178H, m), 3.38 (3H, s).

(29)

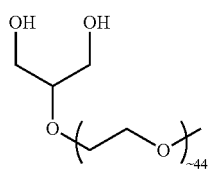

Tetrazole (0.45M in acetonitrile, 10.1 mmol) was added to a solution of dibenzyl N,N-diisopropylphosphoramidite (3.5 g, 10.1 mmol) in methylene chloride (100 mL), and the mixture was stirred at ambient temperature for 30 min. Diol compound 29 was then added (5.0 g, 2.53 mmol) and the resulting mixture was stirred for 48 h at 40° C. The reaction was then cooled to −35° C. and tert-butylhydroperoxide (90%) (0.91 g, 10.1 mmol) was added as a single portion. The reaction mixture was then stirred at −35° C. for 10 minutes, allowed to warm to room temperature, and then stirred for an additional 4 h. A 10% (w/v) aqueous solution of sodium sulfite (100 mL) was then added and the layers were separated. The aqueous layer was back extracted with methylene chloride (100 mL) and the combined organic extracts were evaporated under reduced pressure. The resulting product was utilized without further purification as yellow oil compound 30.

(30)

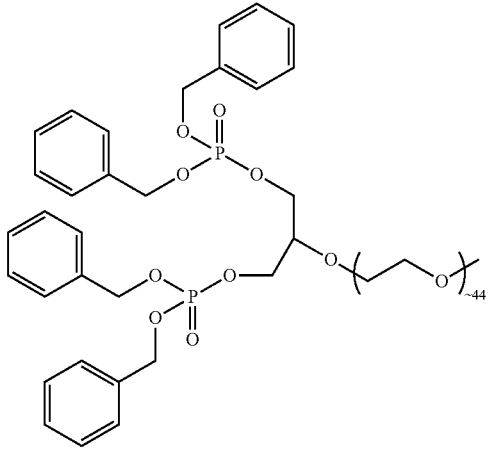

bisdibenzyl phosphate 30 was converted to bisphosphate 31 as taught in Example 13 herein.

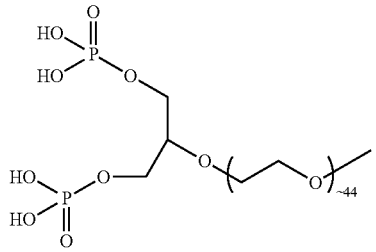
(31)

Comparative Example 1

Synthesis of a PEG2000 monophosphate (33)

A solution of PEG1900 monomethyl ether in methylene chloride containing an excess of triethylamine and catalytic 4-dimethylaminopyridine (DMAP) was treated with an excess of diphenyl chlorophosphate. The mixture was stirred for 24 hours under nitrogen, quenched by the addition of an excess of 1N hydrochloric acid, and the layers were separated. The organic layer was washed once with water, the solvent was distilled off first at atmospheric pressure, then at reduced pressure, to azeoptropically remove any remaining water. The residue was crystallized from a mixture of hot THF and hexanes, then was washed with methyl tert-butyl ether. After drying under vacuum, the product was redissolved in tetrahydrofuran and treated with activated charcoal. The charcoal was filtered off, and the solution was diluted with hexanes, cooled, and the precipitated product collected by filtration. The solids were washed with methyl tert-butyl ether and hexanes, then dried under vacuum for a 70-90% yield of product PEG2000 monophosphate diphenyl ester 32.

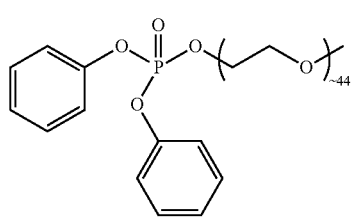
(32)

A solution of the PEG2000 monophosphate diphenyl ester 32 in acetic acid was hydrogenated at 45° C. and 2-4 bar pressure in the presence of 5 mole % platinum oxide until the hydrogen uptake ceased. After cooling, the catalyst was removed by filtration, the filtrate was concentrated under reduced pressure and the residue was dissolved in tetrahydrofuran. Hexanes were added, the mixture was cooled, the precipitated product was collected by filtration, and the solid was washed with methyl tert-butyl ether and hexanes. The product monophosphate 33 was then dried under vacuum at ambient temperatures for a 70-90% yield of product. This material was not stable to autoclave sterilization, whereas the 1,2 and 1,3-BPP2000 materials were shown to be stable under comparable autoclave conditions.

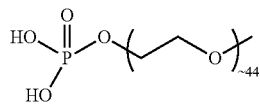
(33)

Comparative Example-2

Synthesis of a PEG2000 Monophosphate Coated SPIO

PEG2000 monophosphate (14.57 g, 7.0 mmol) prepared in Comparative Example 1 was suspended in THF (161 mL) and a solution of SPIO nanoparticles (35 mL at 5.6 mg Fe/mL in benzyl alcohol) was added. The resulting suspension was stirred at 50° C. for 16 h during which the reaction became homogeneous. The reaction was then cooled to room temperature and diluted with water (200 mL). The resulting layers were separated and the aqueous layer was washed with hexanes (2×200 mL). The remaining volatiles were removed from the aqueous layer in vacuo and the resulting aqueous nanoparticle suspension was washed against a 100 kDa MWCO tangential flow filtration membrane with water (3.75 L) to provide a suspension of The resulting nanoparticles had a hydrodynamic diameter of 18.7 nm in 150 mM NaCl at 25° C. as measured by dynamic light scattering.

Comparative Example 3

Autoclave stability of PEG2000 Monophosphate Coated SPIO

A suspension of PEG2000 monophosphate coated SPIO nanoparticles prepared in Comparative Example 2 (1 mL at 10 mg Fe/mL) in water were autoclaved in a closed, 2 dram glass vial at 121° C. and 20 atm for 15 min. After the autoclave cycle was complete, all color had precipitated from the solution, indicating complete aggregation of the nanoparticles.

Comparative Example 4

Synthesis of a PEG350 monophosphate Coated SPIO (XVII)

A solution of PEG-350 mono(methyl ether) (8.54 g, 24.4 mmol) dissolved in $CH_2Cl_2$ (80 mL) was charged with triethyl amine (3.68 g, 36.6 mmol) followed by 4-N,N-dimethylaminopyridine (0.298 g, 2.44 mmol). The resulting solution was cooled to 0° C., diphenyl chlorophosphate (7.87 g, 29.3 mmol) was added dropwise, and the reaction was stirred at 0° C. for 10 min. The reaction was then warmed to room temperature and stirred for an additional 16 h. The reaction was quenched by the addition of 10% HCl (80 mL) and the resulting layers were separated. The organic layer was washed with water (80 mL) and brine (80 mL) and dried over anhydrous $MgSO_4$. Filtration and removal of the solvent in vacuo afforded the mono phosphate diphenyl ester of PEG-350 mono(methyl ether) (14.2 g, 100%) as a golden oil. $^1$H NMR (400 MHz, $CDCl_3$, δ): 7.34 (m, 4H), 7.22 (m, 6H), 4.38 (m, 2H), 3.73 (m, 2H), 3.64 (m, 24H), 3.54 (m, 2H), 3.38 (s, 3H).

Platinium$^{IV}$ oxide hydrate (200 mg) was added to a solution of the mono phosphate diphenyl ester of PEG-350 mono (methyl ether) prepared above (14.2 g, 24.4 mmol) dissolved in acetic acid, and the resulting suspension was heated to 50° C. and placed under an atmosphere of $H_2$ until hydrogen uptake ceased. The reaction was filtered through a celite pad to remove catalyst and the solvent was removed in vacuo to leave the desired product mono phosphate of PEG-350 mono (methyl ether) (10.49 g, 100%) as a clear, yellow oil. $^1$H NMR (400 MHz, CDCl$_3$, δ): 4.20 (m, 2H), 3.67 (m, 24H), 3.56 (m, 2H), 3.39 (s, 3H).

To a colloidal suspension of superparamagnetic iron oxide nanoparticles (SPIO cores solution in benzyl alcohol) diluted to 1 mg Fe/mL with THF was added the mono phosphate of PEG-350 mono(methyl ether) (2 mol of phosphate groups per mol of Fe) and the resulting suspension was heated at 50° C. for 16 h. The reaction was then cooled to room temperature, diluted with water, and the brown aqueous solution was washed three times with hexanes. Any remaining volatiles in the aqueous layer were removed in vacuo and the resulting nanoparticles were purified by washing with H$_2$O against a 30 kDa molecular cutoff filter using tangential flow filtration to provide a suspension of nanoparticle composition XVII. The particles had a hydrodynamic diameter of 50 nm, as measured by dynamic light scattering. After 1 week of storage in water the particles had a hydrodynamic diameter greater than 100 nm.

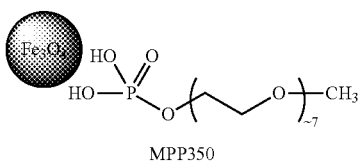

XVII

MPP350

Comparative Example 5

Comparison of Stability of 1,2-bisphosphate, 1,3-bisphosphate, and monophosphate Coated SPIOs Data are gathered in the Table below which compare the properties of nanoparticle compositions provided by the present invention with a nanoparticle composition not comprising a phosphorylated polyol comprising at least two phosphate groups, the PEG-350 phosphate. The effect of a "second" phosphate group is striking in that it renders the nanoparticle composition both more stable in terms if change in hydrodynamic diameter ($D_H$) as determined by dynamic light scattering.

TABLE

Stability and Zeta Potential of Coated SPIOs

| Nanoparticle Coating | $D_H$ post synthesis | $D_H$ 2 weeks post synthesis | Zeta Potential |
| --- | --- | --- | --- |
| PEG-350 Phosphate* | 50 ± 1 nm | >100 nm | 7.3 mV |
| 1,2-BPP350 SPIO† | 9 ± 1 nm | 9 ± 1 nm | −5.0 mV |
| 1,3-BPP350 SPIO† | 9.5 ± 1 nm | 8.4 ± 1 nm | −1.7 mV |

*mono phosphate (also referred to herein as the mono phosphate of PEG-350 mono(methyl ether),
†bisphosphate Additional data are gathered in the following Table which further illustrate the advantages of the nanoparticle compositions provided by the present invention. The data highlight the importance of having at least two phosphate groups present in the phosphorylated polyol used to stabilize the nanoparticulate metal oxide (here nanoparticulate superparamagnetic iron oxide, referred to simply as SPIO or SPIOs) and the advantages provided by stabilizers comprising two phosphate groups and one or more hydrophilic groups of the polyalkylene ether type, for example polyethylene ether groups derived from the mono methyl ether of PEG350 or the mono methyl ether of PEG2000. Significantly, at least some of the nanoparticle compositions provided by the present invention are stable under autoclaving conditions, which characteristic may serve as a threshold indicator of suitability for a material's use in human medical imaging techniques. It is emphasized that the data presented are for nanoparticle compositions comprising the indicated stabilizer compounds as opposed to the stabilizer compounds themselves in the absence of the nanoparticulate metal oxide.

TABLE

Stability of Coated SPIOs As A Function Of Stabilizer Structure

| 1,2-Bisphosphate Stabilizer | Monophosphate Stabilizer |
| --- | --- |
| 1,2-BPP350 | PEG350-monophosphate |
| $D_H$ = 9 nm | $D_H$ = >50 nm |
| Stable in 150 mM saline solution, 2 days at 40° C. | Unstable in 150 mM saline solution, 2 days at 40° C. |
| TFF stable | Unstable to TFF |
| 1,2-BPP2000 | PEG2000-monophosphate |
| $D_H$ = 16 nm | $D_H$ = 22 nm |
| Stable in 150 mM saline solution, 2 days at 40° C. | Stable in 150 mM saline solution, 2 days at 40° C. |
| TFF stable | TFF stable |
| Autoclave stable, 121° C. 15 min | Unstable to autoclave, 121° C. 15 min |

‡Tangential Flow Filtration (purification)

Example 16

In Vivo Imaging of Tumors by MRI

All procedures involving animals were completed under protocols approved by the GE Global Research Institutional Animal Care and Use Committee. Tumors were induced in female Fischer 344 rats (~150 g) by subcutaneous injection of 2×10$^6$ Mat B III cells (ATCC#CRL1666, ATCC, Manassas, Va.) in 0.1 mL Hank's balanced saline solution. The injection site was located dorsally between the shoulder blades. The tumors were imaged 12 days after implantation, when the tumors were ~1 cm in diameter.

Imaging was conducted on a clinical 3 Tesla GE MR750 scanner using a custom-built, ~6 cm solenoid receiver RF coil. To prepare for imaging, the rats were anesthetized by IP injection of ketamine and diazepam using 55 and 3.8 mg/kg doses, respectively. Once immobile, a saline primed 1 F tail vein catheter (MTV-02, Strategic Applications Inc., Libertyville, Ill.) was placed in a lateral tail vein and secured with tape. The prepared animal was then placed within the RF coil and positioned within the bore of the scanner. A pre-injection image set was acquired, and then, without moving the table or the animal, the 1-2 bisphosphate-PEG (Mw=2 kDa) coated superparamagnetic iron oxide nanoparticles were injected via the catheter by a saline flush (~0.4 mL). Following injection, image sets were collected throughout a dynamic acquisition period of ~30 minutes. For the injection, the nanoparticle composition (SPIO agent) was formulated in 5% aqueous mannitol at a concentration of 2 mg Fe/mL and was dosed at 2 mg Fe/kg body weight.

A 3D fast gradient echo pulse sequence was employed that allowed simultaneous collection of images at 10 echo times. The imaging slab was positioned via the graphical prescription interface such that the tumor was centered within the transaxial slices and the coverage included the majority of the tumor in depth. The pulse sequence parameters were as follows: pulse sequence: 3D ME fGRE; TE: ranged from 4.0 to 65.4 ms, with 6.8 ms spacing; TR: 70.4 ms; flip angle: 25 degrees; bandwidth: 62.5 MHz; matrix: 256×192; slice thickness: 0.6 mm; field of view: 9 cm, yielding a voxel size of 0.35×0.35×0.6 mm. The sequence acquisition time was ~2 min.

Figure 2:
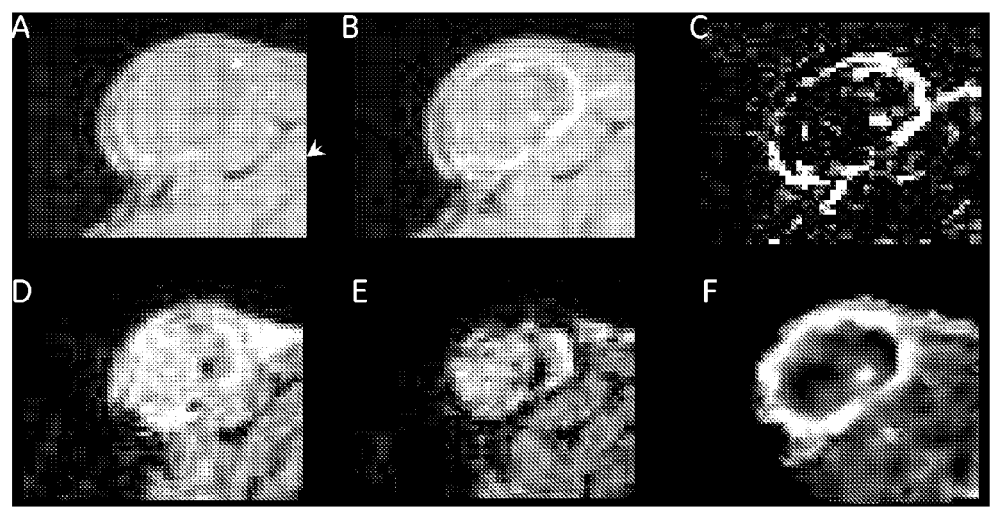
FIG. 2A is a $T_1$ weighted image (TE=4.1 ms) of a tumor in accordance with Example 29, before administration of iron oxide nanoparticle composition.
FIG. 2B is a $T_1$ weighted image (TE=4.1 ms) of a tumor in accordance with Example 29, 30 min after the administration of the nanoparticle contrast agent of Example 10.
FIG. 2C is a difference map of the differences between FIG. 2A and FIG. 2B.
FIG. 2D is a $T_2^*$-weighted image (TE=24.5 ms) of a tumor in accordance with Example 29, before administration of iron oxide nanoparticle composition.
FIG. 2E is a $T_2^*$-weighted image (TE=24.5 ms) of a tumor in accordance with Example 29, 15 min after the administration of the nanoparticle contrast agent of Example 10.
FIG. 2F is an $R_2^*$ relaxation difference map of the differences between FIG. 2D and FIG. 2E exhibiting a clear distinction between tumor and muscle tissue.

The imaging data sets were analyzed using a custom software tool (CineTool v8.0.2, GE Healthcare) built upon the IDL platform (IDL v. 6.3, ITT Corp., Boulder, Colo.). In brief, the image analysis tool allowed manual drawing of 3D regions of in interest (ROIs) on the pre-injection series with subsequent calculation of the $T_2^*$ time constant and extrapolated intensity at TE=0 by exponential regression for every voxel within the drawn ROIs at all time points. These data were used for estimation of physiologic parameters including tumor blood volume and vascular permeability. Representative images and difference maps are given in FIG. 2. The FIG. 2 illustrates the representative T1-weighted images (TE=4.0 ms) before injection of the iron oxide nanoparticle composition (A) and 30 min following injection of the iron oxide nanoparticle composition (B). The tumor region (arrow) shows more enhancement than muscle (arrow head), as demonstrated by signal intensity difference map (C). $T2^*$-weighted images (TE=24.5 ms) for the same slice before administration of iron oxide nanoparticle composition (D) and 15 m following the administration of iron oxide nanoparticle composition (E). Difference map of the $R^{2*}$ relaxation rate (F) exhibits differentiation of tumor from muscle tissue.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A nanoparticle composition comprising:
a nanoparticulate iron oxide core; and
a shell comprising a phosphorylated polyol comprising at least two phosphate groups, wherein at least two of the phosphate groups occupy positions in the phosphorylated polyol which constitute a 1,2 or 1,3 spatial relationship to one another and the polyol comprises a hydrophilic group selected from the group consisting of polyethylene ether moieties, polypropylene ether moieties, polybutylene ether moieties, and combinations of two or more of the foregoing hydrophilic moieties.

2. The composition of claim 1, wherein the nanoparticulate iron oxide core comprises superparamagnetic iron oxide.

3. The composition of claim 1, wherein the phosphorylated polyol comprises at least one of an ester group, amide group, a carbamate group, a urea group, or a carbonate group.

4. The composition of claim 1, characterized by an average hydrodynamic diameter ($D_H$) as determined by dynamic light scattering in 150 mM NaCl water in a range from about 2 nm to about 500 nm.

5. The nanoparticle composition of claim 1, characterized by a zeta potential between about −40 mV and about +40 mV.

6. The composition of claim 1, characterized by its ability to form a stable aqueous colloidal suspension that exhibits no substantial change in hydrodynamic diameter ($D_H$) as determined by dynamic light scattering in 150 mM aqueous NaCl after tangential flow filtration and storage for one week at room temperature.

7. A nanoparticle composition comprising:
a nanoparticulate metal oxide core, wherein the metal oxide comprises a metal selected from the group consisting of iron, tantalum, zirconium, and hafnium; and
a shell comprising a phosphorylated polyol comprising at least two phosphate groups, wherein at least two of the phosphate groups occupy positions in the phosphorylated polyol which constitute a 1,2 or 1,3 spatial relationship to one another and the polyol comprises a hydrophilic group selected from the group consisting of polyethylene ether moieties, polypropylene ether moieties, polybutylene ether moieties, and combinations of two or more of the foregoing hydrophilic moieties.

8. A nanoparticle composition, comprising: a nanoparticle metal oxide; and a phosphorylated polyol comprises one or more hydrophilic groups selected from the group consisting of polyethylene ether moieties, polypropylene ether moieties, polybutylene ether moieties, and combinations of two or more of the foregoing hydrophilic moieties, wherein the phosphorylated polyol has structure V

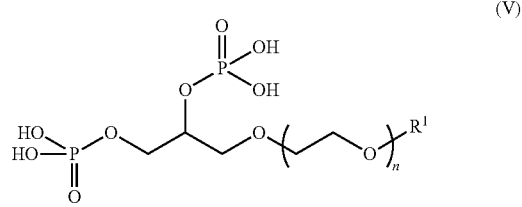

(V)

wherein n is an integer from about 16 to about 150 and $R^1$ is an alkyl group.

* * * * *